US010745336B2

(12) United States Patent
Galvan et al.

(10) Patent No.: US 10,745,336 B2
(45) Date of Patent: Aug. 18, 2020

(54) CYCLOHEXANONE-CONTAINING PRODUCTS AND PROCESSES FOR MAKING THE SAME

(71) Applicant: ExxonMobil Chemical Patents Inc., Baytown, TX (US)

(72) Inventors: Kendele S. Galvan, Houston, TX (US); Christopher L. Becker, Manhattan, KS (US); Jörg F. W. Weber, Houston, TX (US); Ashley J. Malik, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/621,123

(22) PCT Filed: Apr. 24, 2018

(86) PCT No.: PCT/US2018/029091
§ 371 (c)(1),
(2) Date: Dec. 10, 2019

(87) PCT Pub. No.: WO2019/005276
PCT Pub. Date: Jan. 3, 2019

(65) Prior Publication Data
US 2020/0123089 A1 Apr. 23, 2020

Related U.S. Application Data

(60) Provisional application No. 62/525,930, filed on Jun. 28, 2017.

(51) Int. Cl.
*C07C 45/82* (2006.01)
*C07C 45/62* (2006.01)
*C07C 45/00* (2006.01)

(52) U.S. Cl.
CPC ............ *C07C 45/62* (2013.01); *C07C 45/002* (2013.01); *C07C 45/006* (2013.01); *C07C 45/82* (2013.01)

(58) Field of Classification Search
CPC ........ C07C 45/62; C07C 45/002; C07C 45/82
See application file for complete search history.

(56) References Cited

U.S. PATENT DOCUMENTS

| | | |
|---|---|---|
| 3,076,810 A | 2/1963 | Duggan et al. |
| 3,322,651 A | 5/1967 | Nielsen |
| 3,998,884 A | 12/1976 | Gibson |
| 4,021,490 A | 5/1977 | Hudson |
| 4,200,553 A | 4/1980 | Fisher et al. |
| 4,203,923 A | 5/1980 | Ulmer et al. |
| 4,439,409 A | 3/1984 | Puppe et al. |
| 4,826,667 A | 5/1989 | Zones et al. |
| 4,954,325 A | 9/1990 | Rubin et al. |
| 5,064,507 A | 11/1991 | O'Donnell et al. |
| 5,168,983 A | 12/1992 | Tan et al. |
| 5,236,575 A | 8/1993 | Bennett et al. |
| 5,250,277 A | 10/1993 | Kresge et al. |
| 5,362,697 A | 11/1994 | Fung et al. |
| 6,015,927 A | 1/2000 | Kiel et al. |
| 6,037,513 A | 3/2000 | Chang et al. |
| 6,046,365 A | 4/2000 | Kiel et al. |
| 6,077,498 A | 6/2000 | Diaz et al. |
| 6,215,028 B1 | 4/2001 | Oster et al. |
| 6,730,625 B1 | 5/2004 | Chang et al. |
| 6,756,030 B1 | 6/2004 | Rohde et al. |
| 7,199,271 B2 | 4/2007 | Fodor |
| 7,579,506 B2 | 8/2009 | Leconte et al. |
| 7,579,511 B1 | 8/2009 | Dakka et al. |
| 8,178,728 B2 | 5/2012 | Cheng et al. |
| 8,222,459 B2 | 7/2012 | Dakka et al. |
| 8,247,627 B2 | 8/2012 | Dakka et al. |
| 8,389,773 B2 | 3/2013 | Parton et al. |
| 8,618,334 B2 | 12/2013 | Horsels et al. |
| 8,772,550 B2 | 7/2014 | Parton et al. |
| 8,802,897 B2 | 8/2014 | Neumann et al. |
| 8,884,067 B2 | 11/2014 | Kuechler et al. |
| 8,884,068 B2 | 11/2014 | Kuechler et al. |
| 8,921,603 B2 | 12/2014 | Kuechler et al. |
| 9,169,175 B2 | 10/2015 | Kuechler et al. |
| 9,321,709 B2 | 4/2016 | Kuechler et al. |
| 9,868,687 B2 | 1/2018 | Becker et al. |
| 9,926,254 B2 | 3/2018 | Becker et al. |
| 10,233,140 B2 | 3/2019 | Becker et al. |
| 2013/0217921 A1 | 8/2013 | Kuechler et al. |
| 2015/0038747 A1 | 2/2015 | Becker et al. |
| 2017/0204035 A1 | 7/2017 | Becker et al. |

FOREIGN PATENT DOCUMENTS

| | | |
|---|---|---|
| EP | 0 293 032 B1 | 7/1993 |
| EP | 0 606 553 A2 | 7/1994 |

(Continued)

OTHER PUBLICATIONS

Aleandre C. Dimian; Costin Sorin Bildea, Chemical Process Design: Computer-Aided Case Studies, Wiley (2008) pp. 129-172.

(Continued)

*Primary Examiner* — Sikarl A Witherspoon
(74) *Attorney, Agent, or Firm* — Kevin M. Faulkner

(57) ABSTRACT

Disclosed are processes for making cyclohexanone from a feed mixture comprising cyclohexylbenzene, cyclohexanone, phenol, 3-cylclohexenone and optionally 2-cyclohexenone, comprising feeding the feed mixture to a first distillation column and hydrogenating a fraction from the first distillation column in a hydrogenation reactor separate from the first distillation in the presence of a hydrogenation catalyst under hydrogenation conditions. A cyclohexanone-rich upper effluent comprising 3-cyclohexenone and 2-cyclohexenone at low concentrations can be obtained from the first distillation column.

20 Claims, 3 Drawing Sheets

(56) References Cited

FOREIGN PATENT DOCUMENTS

| EP | 1 575 892 B2 | 5/2007 |
|----|---|---|
| JP | 4342156 B2 | 11/2007 |
| WO | 97/17290 A1 | 5/1997 |
| WO | 2010/098916 A2 | 9/2000 |
| WO | 2014/137624 A2 | 9/2014 |
| WO | 2017/023430 A1 | 2/2017 |
| WO | 2019/005273 A1 | 1/2019 |
| WO | 2019/005274 A1 | 1/2019 |

OTHER PUBLICATIONS

Diaz et al., Hydrogenation of phenol in aqueous phase with palladium on activated carbon catalysts, Chem. Eng'g J. (2007) pp. 65-71, vol. 131.

Gonzalez-Velazco et al., Activity and selectivity of palladium catalysts during the liquid-phase hydrogenation of phenol: Influence of temperature and pressure, Industrial & Eng'g Chem. Research, vol. 34, No. 4, Apr. 1995 (Apr. 1, 1995), pp. 1031.

CYCLOHEXANONE-CONTAINING PRODUCTS AND PROCESSES FOR MAKING THE SAME

PRIORITY

This application is a National Phase Application claiming priority to PCT Application Serial No. PCT/US2018/029091, filed Apr. 24, 2018, which claims the benefit of and priority to U.S. Provisional Application No. 62/525,930, filed Jun. 28, 2017, which are incorporated herein by reference.

FIELD

The present invention relates to processes for making cyclohexanone and cyclohexanone-containing products. In particular, the present invention relates to processes for making cyclohexanone including a step of abating 3-cyclohexenone from a process stream, and cyclohexanone-containing products thus made. The present invention is useful, e.g., in making cyclohexanone from cyclohexylbenzene oxidation and cyclohexylbenzene hydroperoxide cleavage.

BACKGROUND

Cyclohexanone is an important material in the chemical industry and is widely used in, for example, production of phenolic resins, bisphenol A, caprolactam, adipic acid, and plasticizers. One method for making cyclohexanone is by hydrogenating phenol.

Currently, a common route for the production of phenol is the Hock process. This is a three-step process in which the first step involves alkylation of benzene with propylene to produce cumene, followed by oxidation of cumene to the corresponding hydroperoxide, and then cleavage of the hydroperoxide to produce equimolar amounts of phenol and acetone. The separated phenol product can then be converted to cyclohexanone by a step of hydrogenation.

It is known from, e.g., U.S. Pat. No. 6,037,513, that cyclohexylbenzene can be produced by contacting benzene with hydrogen in the presence of a bifunctional catalyst comprising a molecular sieve of the MCM-22 type and at least one hydrogenation metal selected from palladium, ruthenium, nickel, cobalt, and mixtures thereof. This reference also discloses that the resultant cyclohexylbenzene can be oxidized to the corresponding hydroperoxide, which can then be cleaved to produce a cleavage mixture of phenol and cyclohexanone, which, in turn, can be separated to obtain pure, substantially equimolar phenol and cyclohexanone products. This cyclohexylbenzene-based process for co-producing phenol and cyclohexanone can be highly efficient in making these two important industrial materials. Given the higher commercial value of cyclohexanone than phenol, it is highly desirable that in this process more cyclohexanone than phenol be produced. While this can be achieved by subsequently hydrogenating the pure phenol product produced in this process to convert a part or all of the phenol to cyclohexanone, a more economical process and system would be highly desirable.

One solution to making more cyclohexanone than phenol from the above cyclohexylbenzene-based process is to hydrogenate a mixture containing phenol and cyclohexanone obtained from the cleavage mixture to convert at least a portion of the phenol contained therein to cyclohexanone. However, because the phenol/cyclohexanone mixture invariably contains non-negligible amounts of (i) catalyst poison component(s) (such as S-containing components) that can poison the hydrogenation catalyst, and (ii) cyclohexylbenzene that can be converted into bicyclohexane in the hydrogenation step, and because hydrogenation of the phenol/cyclohexanone/cyclohexylbenzene mixture can also lead to the formation of cyclohexanol, resulting in yield loss, this process is not without challenge. In short, the unconventional feed to a phenol hydrogenation process, produced by the aforementioned route including hydroalkylation of benzene, presents a great deal of challenges to maintaining the desired activity of phenol hydrogenation catalyst, and the desired selectivity to cyclohexanone.

Recently, the present inventors have found that, in the process including cyclohexylbenzene oxidation followed by acid cleavage of the cyclohexylbenzene hydroperoxide process for making cyclohexanone (hereinafter called the "CHB-route"), 2-cyclohexenone and 3-cyclohexenone are produced due to various side reactions that may occur in the various reactors, especially the cleavage reactor, and one or both of them can be present as impurities in the cyclohexanone-containing products. The presence of 2-cyclohexenone and 3-cyclohexenone impurities at elevated concentrations can cause various issues in downstream use of the cyclohexanone-containing products, such as the manufacture of caprolactam. Therefore, there is a need to abate the concentration of both 2-cyclohexenone and 3-cyclohexenone from the cyclohexanone product.

Some references of potential interest in this regard may include: U.S. Pat. Nos. 3,076,810; 3,322,651; 3,998,884; 4,021,490; 4,200,553; 4,203,923; 4,439,409; 4,826,667; 4,954,325; 5,064,507; 5,168,983; 5,236,575; 5,250,277; 5,362,697; 6,015,927; 6,037,513; 6,046,365; 6,077,498; 6,215,028; 6,730,625; 6,756,030; 7,199,271; 7,579,506; 7,579,511; 8,222,459; 8,389,773; 8,618,334; 8,772,550; 8,802,897; and 8,921,603. Other references of potential interest include WIPO Publication Nos. WO 97/17290; WO 2009/128984; WO 2009/131769; WO 2009/134514; WO 2010/098916; WO 2012/036820; WO 2012/036822; WO 2012/036823; WO 2012/036828; WO 2012/036830; WO 2014/137624, and WO 2017/023430. Further references of potential interest include EP 0 293 032; EP 0 606 553; EP 1 575 892; JP 434156 B2; as well as Alexandre C. Dimian and Costin Sorin Bildea, *Chemical Process Design: Computer-Aided Case Studies*, pp. 129-172 (Wiley, 2008); Van Peppen, J. F. et al., *Phenol Hydrogenation Process*, in Catalysis of Organic Reactions, pp. 355-372 (1985, ed. R. L. Augustine); Diaz et al., *Hydrogenation of phenol in aqueous phase with palladium on activated carbon catalysts*, CHEM. ENG'G J. 131 (2007) at 65-71; and Gonzalez-Velazco et al., *Activity and selectivity of palladium catalysts during the liquid-phase hydrogenation of phenol: Influence of temperature and pressure*, INDUSTRIAL & ENG'G CHEM. RESEARCH (April 1995), Vol. 34, No. 4, p. 1031.

SUMMARY

It has been found that, by subjecting process streams containing cyclohexanone and 3-cyclohexenone and optionally 2-cyclohexenone through a hydrogenation step, such as hydrogenation process designed for hydrogenating phenol, one can successfully hydrogenate 2-cyclohexenone and 3-cyclohexenone at a high level of conversion, effectively abating the concentrations of 2-cyclohexenone and 3-cyclohexenone in the process stream to a low level. From the abated process stream, one can obtain a cyclohexanone-containing product depleted of both 2-cyclohexenone and 3-cyclohexenone.

Thus, a first aspect of the present disclosure relates to a process for producing cyclohexanone from a first feed mixture comprising cyclohexylbenzene, cyclohexanone, phenol, and 3-cyclohexenone, the process comprising: feeding the first feed mixture into a first distillation column at a first feeding location; obtaining a lower cyclohexylbenzene-rich effluent from a location in the vicinity of the bottom of the first distillation column; obtaining a first upper effluent from a first upper effluent location on the first distillation column above the first feeding location, the first upper effluent comprising cyclohexanone and cyclohexanol, and being substantially free of phenol and 3-cyclohexenone; obtaining a middle effluent from a middle effluent location on the first distillation column above the first feeding location and below the first upper effluent location, the middle effluent comprising cyclohexanone, phenol, and 3-cyclohexenone; feeding at least a portion of the middle effluent to a hydrogenation reactor, where the middle effluent contacts with hydrogen in the presence of a hydrogenation catalyst under hydrogenation conditions to produce a hydrogenation reactor effluent substantially free of 3-cylcohexenone; feeding at least a portion of the hydrogenation reactor effluent to the first distillation column at a recycle location between the middle effluent location and the first upper effluent location, wherein: (i) the recycle location is 6 to 30 stages above the middle effluent location; and (ii) the conversion of phenol in the hydrogenation reactor is no higher than 99%.

A second aspect of the present disclosure relates to a cyclohexanone-containing product substantially free of phenol and comprising, based on the total weight thereof: at least 10 wt % of cyclohexanone; 0 to 90 wt % of cyclohexanol; 0.01 to 20 ppm by weight of 3-cyclohexenone; and optionally 0.01 to 20 ppm by weight of 2-cyclohexenone.

DETAILED DESCRIPTION

Figure 1:
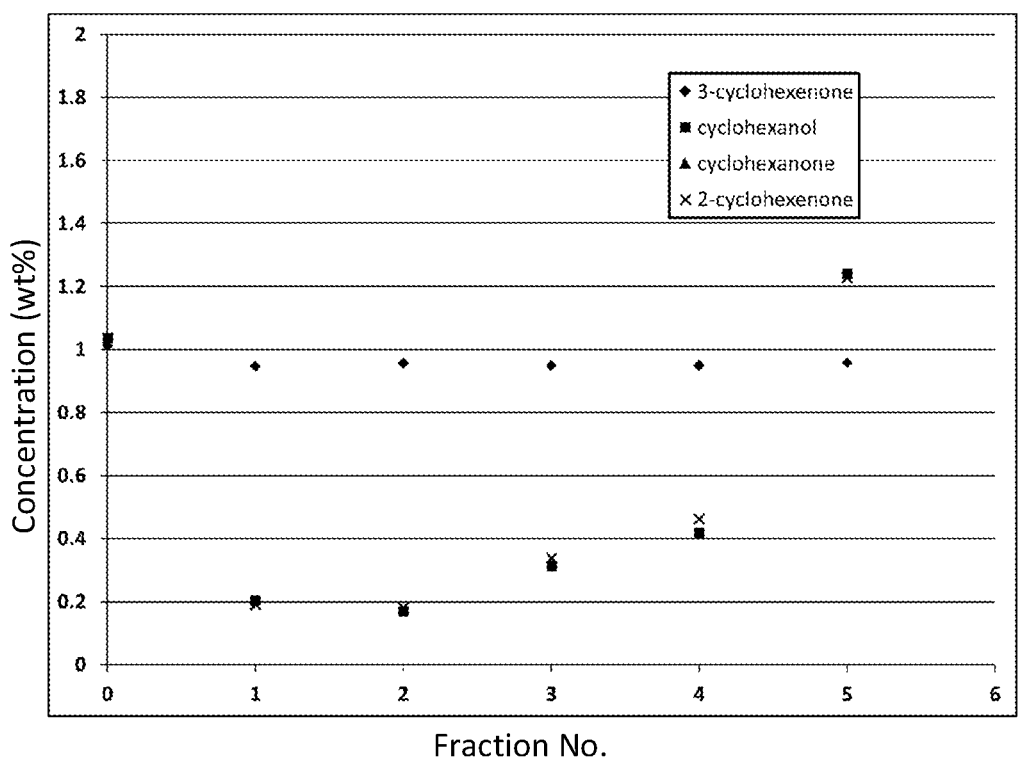
FIG. 1 is a schematic diagram showing the concentrations of 2-cyclohexenone, 3-cyclohexenone, and cyclohexanol of various fractions obtained from spinning band distillation ("SBD") of a feed mixture consisting of 2-cyclohexenone, 3-cyclohexenone, cyclohexanol, and cyclohexanone.

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, steps in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

I. Definitions

As used herein, the indefinite article "a" or "an" shall mean "at least one" unless specified to the contrary or the context clearly indicates otherwise. Thus, embodiments comprising "a light component" include embodiments where one, two or more light components exist, unless specified to the contrary or the context clearly indicates that only one light component exists.

A "complex" as used herein means a material formed by identified components via chemical bonds, hydrogen bonds, and/or physical forces.

An "operation temperature" of a distillation column means the highest temperature liquid media inside the column is exposed to during normal operation. Thus, the operation temperature of a column is typically the temperature of the liquid media in the reboiler, if the column is equipped with a reboiler.

The term "S-containing component" as used herein includes all compounds comprising sulfur.

In the present application, sulfur concentration in a material is expressed in terms of proportion (ppm, weight percentages, and the like) of the weight of elemental sulfur relative to the total weight of the material, even though the sulfur may be present in various valencies other than zero. Sulfuric acid concentration is expressed in terms of proportion (ppm, weight percentages, and the like) of the weight of $H_2SO_4$ relative to the total weight of the material, even though the sulfuric acid may be present in the material in forms other than $H_2SO_4$. Thus, the sulfuric acid concentration is the total concentration of $H_2SO_4$, $SO_3$, $HSO_4^-$, and R—$HSO_4$ in the material.

As used herein, "wt %" means percentage by weight, "vol %" means percentage by volume, "mol %" means percentage by mole, "ppm" means parts per million, and "ppm wt" and "ppm by weight" are used interchangeably to mean parts per million on a weight basis. All "ppm" as used herein are ppm by weight unless specified otherwise. All concentrations herein are expressed on the basis of the total amount of the composition in question, unless otherwise noted. Thus, absent a contrary indication, the concentrations of the various components of a first mixture are expressed based on the total weight of the first mixture. All ranges expressed herein should include both end points as two specific embodiments unless specified or indicated to the contrary.

In the present disclosure, a location "in the vicinity of" an end (top or bottom) of a column means a location within 10% of the top or bottom, respectively, the % being based upon the total height of the column. That is, a location "in the vicinity of the bottom" of a column is within the bottom 10% of the column's height, and a location "in the vicinity of the top" of a column is within the top 10% of the column's height.

An "upper effluent" as used herein may be at the very top or the side of a vessel such as a distillation column or a reactor, with or without an additional effluent above it. Preferably, an upper effluent is drawn at a location in the vicinity of the top of the column. Preferably, an upper effluent is drawn at a location above at least one feed. A "lower effluent" as used herein is at a location lower than the upper effluent, which may be at the very bottom or the side of a vessel, and if at the side, with or without additional effluent below it. Preferably, a lower effluent is drawn at a location in the vicinity of the bottom of the column. Preferably, a lower effluent is drawn at a location below at least one feed. As used herein, a "middle effluent" is an effluent between an upper effluent and a lower effluent. The "same level" on a distillation column means a continuous segment of the column with a total height no more than 5% of the total height of the column. In the present disclosure, the term "fraction" and "effluent" are used interchangeably.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, 6$^{th}$ Edition, by F. Albert Cotton et al. (John Wiley & Sons, Inc., 1999).

As used herein, the term "methylcyclopentanone" includes both isomers 2-methylcyclopentanone (CAS Registry No. 1120-72-5) and 3-methylcyclopentanone (CAS Registry No. 1757-42-2), at any proportion between them, unless it is clearly specified to mean only one of these two isomers or the context clearly indicates that is the case. It should be noted that under the conditions of the various steps of the present processes, the two isomers may undergo isomerization reactions to result in a ratio between them different from that in the raw materials immediately before being charged into a vessel such as a distillation column.

As used herein, the generic term "dicyclohexylbenzene" ("Dicyclohexylbenzene") includes, in the aggregate, 1,2-dicyclohexylbenzene, 1,3-dicylohexylbenzene, and 1,4-dicyclohexylbenzene, unless clearly specified to mean only one or two thereof. The term cyclohexylbenzene, when used in the singular form, means mono substituted cyclohexyl-benzene. As used herein, the term "C12" means compounds having 12 carbon atoms, and "C12+ components" means compounds having at least 12 carbon atoms. Examples of C12+ components include, among others, cyclohexylbenzene, biphenyl, bicyclohexane, methylcyclopentylbenzene, 1,2-biphenylbenzene, 1,3-biphenylbenzene, 1,4-biphenylbenzene, 1,2,3-triphenylbenzene, 1,2,4-triphenylbenzene, 1,3,5-triphenylbenzene, and corresponding to oxygenates such as alcohols, ketones, acids, and esters derived from these compounds. As used herein, the term "C18" means compounds having 18 carbon atoms, and the term "C18+ components" means compounds having at least 18 carbon atoms. Examples of C18+ components include, among others, dicyclohexylbenzenes ("Dicyclohexylbenzene," described above), tricyclohexylbenzenes ("Tricyclohexylbenzene," including all isomers thereof, including 1,2,3-tricyclohexylbenzene, 1,2,4-tricyclohexylbenzene, 1,3,5-tricyclohexylbenzene, and mixtures of two or more thereof at any proportion). As used herein, the term "C24" means compounds having 24 carbon atoms.

In the present disclosure, when the word "rich" is used in describing a component in a given effluent or a mixture produced from a vessel, reactor or distillation column, it means the concentration of the component in that given effluent or mixture is higher than its concentration in a feed supplied into the vessel, reactor or distillation column.

In the present disclosure, when the word "depleted" is used in describing a component in a given effluent or a mixture produced from a vessel, reactor or distillation column, it means the concentration of the component in that given effluent or mixture is lower than its concentration in a feed supplied into the vessel, reactor or distillation column.

In the present disclosure, the term "light components" means components having a normal boiling point lower than cyclohexanone.

In the present disclosure, the term "light acid" means acid having a normal boiling point lower than cyclohexanone.

In the present disclosure, the term "substantially free of phenol" means comprising phenol at a concentration no higher than 100 (preferably no higher than 50, still more preferably no higher than 20, still more preferably no higher than 10) ppm by weight, based on the total weight of the material in question.

As used herein, the term "2-cyclohexenone" means a compound having the formula:

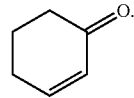

2-cyclohexenone can be separated from cyclohexanone by conventional distillation, as demonstrated in Example 1 herein. 2-cyclohexenone, if included in a cyclohexanone product at elevated concentrations, can cause problems in downstream use of the product, e.g., in making caprolactam used for making nylon-6, a commercially important polyamide. Thus, it is highly desirable that a cyclohexanone product contain 2-cyclohexenone at a low concentration, e.g., no higher than 100, 80, 60, 50, 40, 30, 20, or 10, ppm by weight, based on the total weight of the product. For the purpose of the present disclosure, a composition of matter comprising 2-cyclohexenone at a concentration no higher than 20 ppm is considered as "substantially free" of 2-cyclohexenone.

As used herein, the term "3-cyclohexenone" means a compound having the formula:

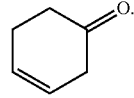

To the surprise of the inventors, 3-cyclohexenone, although a structural isomer of 2-cyclohexenone, cannot be completely separated from cyclohexanone by conventional distillation, as demonstrated in Example 1 herein. Likewise, 3-cyclohexenone, if included in a cyclohexanone product at elevated concentrations, can cause problems in downstream use of the product, e.g., in making caprolactam. Thus, it is highly desirable that a cyclohexanone product contain 3-cyclohexenone at a low concentration, e.g., no higher than 100, 80, 60, 50, 40, 30, 20, or 10, ppm by weight, based on the total weight of the product. Without intending to be bound by a particular theory, it is believed that the difference in behaviors of 2-cyclohexenone and 3-cyclohexenone in their mixtures with cyclohexanone can be explained by the location of the C=C bond relative to the C=O bond in the molecules. In 2-cyclohexenone, the two double bonds are conjugated, while in 3-cyclohexenone, they are not, leading to significantly different affinity to cyclohexanone. For the purpose of the present disclosure, a composition of matter comprising 3-cyclohexenone at a concentration no higher than 20 ppm is considered as "substantially free" of 3-cyclohexenone.

II. General Description of Hydrogenation of Feed Mixture Comprising Cyclohexanone and 3-Cyclohexenone Since simple conventional distillation cannot be used to completely separate 3-cyclohexenone from cyclohexanone, the present inventors contemplated specialized distillation approaches and chemical approaches to abate the 3-cyclohexenone concentration in a cyclohexanone-containing feed mixture. An exemplary specialized distillation process is illustrated in Example 5 herein. One particularly effective chemical approach is hydrogenation of the 3-cyclohexenone and cyclohexanone-containing feed mixture: contacting the feed mixture with hydrogen in the presence of a hydrogenation catalyst under hydrogenation conditions. The C=C bond in the 3-cyclohexenone molecule can be conveniently saturated to produce cyclohexanone, thereby converting 3-cyclohexenone as a contaminant into the desirable product. If the feed mixture also contains 2-cyclohexenone, which can be the case if the feed mixture is prepared via the CHB-route for making cyclohexanone and/or phenol as described in detail below, the 2-cyclohexenone can be converted into cyclohexanone as well. Hydrogenation conditions can be chosen such that the conversion of 3-cyclohexenone and/or 2-cyclohexenone can be up to 80%, 85%, 90%, 95%, 96%, 97%, 98%, 99%, or even 99.9%, or even higher, resulting in a hydrogenated mixture depleted of 2-cyclohexenone and 3-cyclohexenone, comprising each at a concentration no higher than 100, 80, 60, 50, 40, 30, 20, 10, 8, 6, 5, 4, 2, 1, 0.8, 0.6, 0.5, 0.4, 0.2, 0.1, 0.08, 0.06, 0.05, 0.04, 0.02, or even 0.01 ppm by weight based on the total weight of the hydrogenated mixture. It is also possible to achieve a total concentration of 2-cyclohexenone and 3-cyclohexenone combined of no higher than 100, 80, 60, 50, 40, 30, 20, 10, 8, 6, 5, 4, 2, 1, 0.8, 0.6, 0.5, 0.4, 0.2, 0.1, 0.08, 0.06, 0.05, 0.04, 0.02, or even 0.01 ppm by weight based on the total weight of the hydrogenated mixture. The hydrogenated mixture, if comprising substantially only cyclohexanone and preferably substantially free of 2-cyclohexenone and 3-cyclohexenone, can then be used as is without the issues caused by 2-cyclohexenone and 3-cyclohexenone; and if comprising cyclohexanone at a relatively low concentration, can then be separated by conventional distillation to make a high-purity cyclohexanone product depleted of 2-cyclohexenone and 3-cyclohexenone, preferably substantially free of 2-cyclohexenone and 3-cyclohexenone.

Desirably, the feed mixture fed into the hydrogenation step comprises one or both of the 2-cyclohexenone and 3-cyclohexenone each at a relatively low concentration, each independently from a1 to a2 ppm by weight, based on the total weight of the feed mixture, where a1 and a2 can be, independently, 10, 20, 30, 40, 50, 80, 100, 200, 400, 500, 600, 800, 1000, 2000, 4000, 5000, 6000, 8000, $1 \times 10^4$, $2 \times 10^4$, $4 \times 10^4$, $5 \times 10^4$, $6 \times 10^4$, $8 \times 10^4$, $1 \times 10^5$, $2 \times 10^5$, $4 \times 10^5$, $5 \times 10^5$, $6 \times 10^5$, $8 \times 10^5$, $1 \times 10^6$, $2 \times 10^6$, $4 \times 10^6$, $5 \times 10^6$, as long as a1<a2. Preferably a1=50, a2=2000. More preferably a1=100, a2=1000.

The feed mixture undergoing the hydrogenation step may comprise cyclohexanone at a concentration in the range from b1 to b2 wt %, based on the total weight of the feed mixture, where b1 and b2 can be, independently, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, or 99, as long as b1<b2. Some of the cyclohexanone may also undergo hydrogenation in the process to produce cyclohexanol. The quantity of cyclohexanol produced in the hydrogenation step can be controlled by selecting the catalyst and hydrogenation conditions such as temperature, residence time, and hydrogen partial pressure, depending on the exact make-up of the feed mixture. Cyclohexanol can form a mixture with cyclohexanone to obtain KA oil, a saleable product useful for making adipic acid, which, in turn, can be used for making nylon-6,6, another commercially significant polyamide.

The feed mixture undergoing the hydrogenation step can advantageously comprise phenol at a concentration in the range from c1 to c2 wt %, based on the total weight of the feed mixture, where c1 and c2 can be, independently, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, or 98, as long as c1<c2. Desirably, in the hydrogenation step, at least a portion of the phenol included in the feed mixture is also hydrogenated to form cyclohexanone. Desirably, the conversion of phenol in the hydrogenation step is in a range from d1% to d2%, where d1 and d2 can be, independently, 40, 45, 50, 55, 60, 65, 70, 75, 80, 85, 90, 91, 92, 93, 94, 95, 96, 97, 98, or 99, as long as d1<d2. Thus, in the hydrogenation step, phenol, 2-cyclohexenone, and 3-cyclohexenone can all be advantageously converted to cyclohexanone, the desired product.

It has been found that, surprisingly, in a hydrogenation reactor loaded with a hydrogenation catalyst and operating under hydrogenation conditions conducive to converting at least a portion of phenol to cyclohexanone, the reaction rates of 2-cyclohexenone hydrogenation and 3-cyclohexenone hydrogenation to form cyclohexanone are much faster than the reaction of phenol hydrogenation to form cyclohexanone. As such, as long as phenol is converted into cyclohexanone at a significant conversion (e.g., at least 20, 30, 40, 50, or 60 percent), the conversion of 2-cyclohexenone and 3-cyclohexenone tend to be much higher, reaching at least 90, 91, 92, 93, 94, 95, 96, 97, 98, 99, 99.9, or even 99.99 percent, or even higher, resulting in substantially total depletion of 2-cyclohexenone and 3-cyclohexenone in the hydrogenated mixture at the exceedingly low concentrations as described above.

The feed mixture may also comprise cyclohexanol at a concentration in the range from d1 to d2 wt %, based on the total weight of the feed mixture, where d1 and d2 can be, independently, 0.1, 0.5, 1, 5, 10, 15, 20, 25, 30, 35, 40, 45, 50, 55, 60, 65, 70, 75, 80, as long as d1<d2.

An exemplary feed mixture that can be produced from the CHB-route described in detail below can comprise cyclohexanone at a concentration in the range from 1 to 50 wt % (preferably 2 to 40 wt %, more preferably 3 to 30 wt %, still more preferably 5 to 25 wt %), phenol at a concentration from 1 to 90 wt % (preferably 10 to 90 wt %, more preferably 20 to 90 wt %, still more preferably 30 to 90 wt %, still more preferably 40 to 90 wt %, still more preferably 50 to 90 wt %), cyclohexanol from 0 to 50 wt % (preferably 0 to 40 wt %, more preferably 0 to 30 wt %, still more preferably 0 to 20 wt %, still more preferably 0 to 10 wt %, still more preferably 0 to 5 wt %), 3-cyclohexenone at a concentration in the range from 30 to 2000 ppm (preferably 50 to 1000 ppm), and optionally 2-cyclohexenone at a concentration in the range from 30 to 2000 ppm (preferably 50 to 1000 ppm), based on the total weight of the feed mixture. The hydrogenated mixture resulting from this feed mixture can comprise cyclohexanone at a concentration in the range from 5 to 99.99 wt %, 3-cyclohexenone at a concentration in the range from 0.01 to 20 ppm (preferably from 0.01 to 10 ppm), and 2-cyclohexenone at a concentration in the range from 0.01 to 20 ppm (preferably from 0.01 to 10 ppm), based on the total weight of the hydrogenated mixture.

Hydrogenation catalyst suitable for the hydrogenation step typically comprises a hydrogenation metal such as Fe, Co, Ni, Ru, Rh, Pd, Ag, Re, Os, Ir, and Pt, and mixtures and combinations of one or more thereof. Pd is a particularly preferred hydrogenation metal according to some embodiments. Additional details of the hydrogenation catalyst are given later in the present disclosure. The hydrogenation conditions can be chosen such that (i) at least 80% of cyclohexanone is present in liquid phase ("liquid-phase hydrogenation"), or at least 80% of cyclohexanone is present in vapor phase ("vapor-phase hydrogenation"), or more than 20% and less than 80% of cyclohexanone is present in liquid phase ("mixed-phase hydrogenation"). In general, the reaction temperature is in the range from 25 to 300° C. (e.g., from 40 to 250, or from 50 to 200° C.), and the absolute hydrogen partial pressure can be in the range from 50 to 2000 kPa (e.g., from 60 to 1000 kPa, or from 80 to 800 kPa, or from 90 to 600 kPa, or from 100 to 500 kPa).

The general approach of subjecting the feed mixture to a hydrogenation step can be used to abate 3-cyclohexenone and/or 2-cyclohexenone contained in any cyclohexanone-containing materials, irrespective of the specific method of making.

III. The CHB-Route for Making Cyclohexanone and/or Phenol

The CHB-route for making cyclohexanone and/or phenol starts with a step of making cyclohexylbenzene from benzene and hydrogen in the presence of a hydroalkylation catalyst. The cyclohexylbenzene thus produced is then oxidized to form its hydroperoxide, which is then subject to a cleavage reaction in the presence of an acid catalyst to obtain cyclohexanone and phenol. Various separation and purification process can be carried out subsequently to obtain high-purity cyclohexanone and phenol as products, or at least a portion of the phenol can be hydrogenated to make additional cyclohexanone and optionally cyclohexanol. The CHB-route can produce multiple feed mixture containing both cyclohexanone and 3-cyclohexenone and optionally 2-cyclohexenone at various concentrations. The process and system of the present disclosure can be advantageously used to abate the concentration of 3-cyclohexenone and 2-cyclohexenone in those feed mixtures. Detailed description of the process steps of the CHB-route follows.

III.1 Supply of Cyclohexylbenzene

The cyclohexylbenzene supplied to the oxidation step can be produced and/or recycled as part of an integrated process for producing phenol and cyclohexanone from benzene. In such an integrated process, benzene is initially converted to cyclohexylbenzene by any conventional technique, including oxidative coupling of benzene to make biphenyl followed by hydrogenation of the biphenyl. However, in practice, the cyclohexylbenzene is desirably produced by contacting benzene with hydrogen under hydroalkylation conditions in the presence of a hydroalkylation catalyst whereby benzene undergoes the followincg Reaction-1 to produce cyclohexylbenzene:

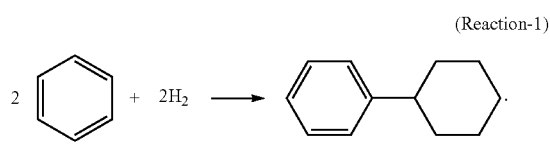 [SMILES: c1ccccc1 ; c1ccc(C2CCCCC2)cc1]

(Reaction-1)

Alternatively, cyclohexylbenzene can be produced by direct alkylation of benzene with cyclohexene in the presence of a solid-acid catalyst such as molecular sieves in the MCM-22 family according to the following Reaction-2:

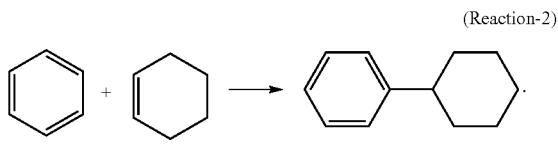

(Reaction-2)

Side reactions may occur in Reaction-1 or Reaction-2 to produce some polyalkylated benzenes, such as dicyclohexylbenzenes (Dicyclohexylbenzene), tricyclohexylbenzenes (Tricyclohexylbenzene), methylcyclopentylbenzene, unreacted benzene, cyclohexane, bicyclohexane, biphenyl, and other contaminants. Thus, typically, after the reaction, the hydroalkylation reaction product mixture is separated by distillation to obtain a C6 fraction containing benzene, cyclohexane, a C12 fraction containing cyclohexylbenzene and methylcyclopentylbenzene, and a heavies fraction containing, e.g., C18s such as Dicyclohexylbenzenes and C24s such as Tricyclohexylbenzenes. The unreacted benzene may be recovered by distillation and recycled to the hydroalkylation or alkylation reactor. The cyclohexane may be sent to a dehydrogenation reactor, with or without some of the residual benzene, and with or without co-fed hydrogen, where it is converted to benzene and hydrogen, which can be recycled to the hydroalkylation/alkylation step. Depending on the quantity of the heavies fraction, it may be desirable to either (a) transalkylate the C18s such as Dicyclohexylbenzene and C24s such as Tricyclohexylbenzene with additional benzene or (b) dealkylate the C18s and C24s to maximize the production of the desired monoalkylated species.

Details of feed materials, catalyst used, reaction conditions, and reaction product properties of benzene hydroalkylation, and transalkylation and dealkylation can be found in, e.g., the following copending, co-assigned patent applications: U.S. Provisional Patent Application Serial Nos. 61/972,877, entitled "Process for Making Cyclohexylbenzene and/or Phenol and/or Cyclohexanone;" and filed on Mar. 31, 2014; U.S. Provisional Patent Application Ser. No.

62/037,794, entitled "Process and System for Making Cyclohexanone," and filed on Aug. 15, 2014; U.S. Provisional Patent Application Ser. No. 62/037,801, entitled "Process and System for Making Cyclohexanone," and filed on Aug. 15, 2014; U.S. Provisional Patent Application Ser. No. 62/037,814, entitled "Process and System for Making Cyclohexanone," and filed on Aug. 15, 2014; U.S. Provisional Patent Application Ser. No. 62/037,824, entitled "Process and System for Making Cyclohexanone," and filed on Aug. 15, 2014; U.S. Provisional Patent Application Ser. No. 62/057,919, entitled "Process for Making Cyclohexanone," and filed on Sep. 30, 2014; U.S. Provisional Patent Application Ser. No. 62/057,947, entitled "Process for Making Cyclohexanone," and filed on Sep. 30, 2014; and U.S. Provisional Patent Application Ser. No. 62/057,980, entitled "Process for Making Cyclohexanone," and filed on Sep. 30, 2014, the contents of all of which are incorporated herein by reference in their entirety.

III.2 Oxidation of Cyclohexylbenzene

In the oxidation step, at least a portion of the cyclohexylbenzene contained in the oxidation feed is converted to cyclohexyl-1-phenyl-1-hydroperoxide, the desired hydroperoxide, according to the following Reaction-3:

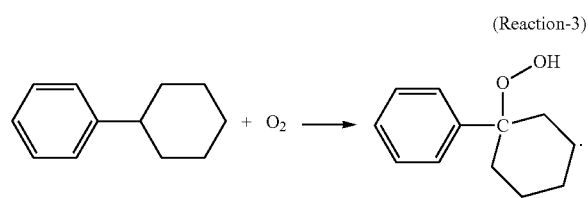

(Reaction-3)

The cyclohexylbenzene freshly produced and/or recycled may be purified before being fed to the oxidation step to remove at least a portion of, among others, methylcyclopentylbenzene, olefins, phenol, acid, and the like. Such purification may include, e.g., distillation, hydrogenation, caustic wash, and the like.

In exemplary processes, the oxidation step may be accomplished by contacting an oxygen-containing gas, such as air and various derivatives of air, with the feed comprising cyclohexylbenzene. For example, a stream of pure $O_2$, $O_2$ diluted by inert gas such as $N_2$, pure air, or other $O_2$-containing mixtures can be pumped through the cyclohexylbenzene-containing feed in an oxidation reactor to effect the oxidation.

The oxidation may be conducted in the absence or presence of a catalyst, such as a cyclic imide type catalyst (e.g., N-hydroxyphthalimide).

Details of the feed material, reaction conditions, reactors used, catalyst used, product mixture composition and treatment, and the like, of the oxidation step can be found in, e.g., the following copending, co-assigned patent applications: U.S. Provisional Patent Application Serial Nos. 61/972,877, entitled "Process for Making Cyclohexylbenzene and/or Phenol and/or Cyclohexanone;" and filed on Mar. 31, 2014; U.S. Provisional Patent Application Ser. No. 62/037,794, entitled "Process and System for Making Cyclohexanone," and filed on Aug. 15, 2014; U.S. Provisional Patent Application Ser. No. 62/037,801, entitled "Process and System for Making Cyclohexanone," and filed on Aug. 15, 2014; U.S. Provisional Patent Application Ser. No. 62/037,814, entitled "Process and System for Making Cyclohexanone," and filed on Aug. 15, 2014; U.S. Provisional Patent Application Ser. No. 62/037,824, entitled "Process and System for Making Cyclohexanone," and filed on Aug. 15, 2014; U.S. Provisional Patent Application Ser. No. 62/057,919, entitled "Process for Making Cyclohexanone," and filed on Sep. 30, 2014; U.S. Provisional Patent Application Ser. No. 62/057,947, entitled "Process for Making Cyclohexanone," and filed on Sep. 30, 2014; and U.S. Provisional Patent Application Ser. No. 62/057,980, entitled "Process for Making Cyclohexanone," and filed on Sep. 30, 2014, the contents of all of which are incorporated herein by reference in their entirety.

III.3 Cleavage Reaction

In the cleavage reaction, at least a portion of the cyclohexyl-1-phenyl-1-hydroperoxide decomposes in the presence of an acid catalyst in high selectivity to cyclohexanone and phenol according to the following desired Reaction-4:

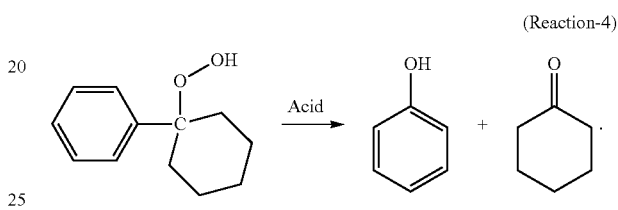

(Reaction-4)

The cleavage product mixture may comprise the acid catalyst, phenol, cyclohexanone, cyclohexylbenzene, and contaminants such as 3-cyclohexenone and optionally 2-cyclohexenone.

The acid catalyst can be at least partially soluble in the cleavage reaction mixture, is stable at a temperature of at least 185° C. and has a lower volatility (higher normal boiling point) than cyclohexylbenzene.

Feed composition, reaction conditions, catalyst used, product mixture composition and treatment thereof, and the like, of this cleavage step can be found in, e.g., the following copending, co-assigned patent applications: U.S. Provisional Patent Application Serial Nos. 61/972,877, entitled "Process for Making Cyclohexylbenzene and/or Phenol and/or Cyclohexanone;" and filed on Mar. 31, 2014; U.S. Provisional Patent Application Ser. No. 62/037,794, entitled "Process and System for Making Cyclohexanone," and filed on Aug. 15, 2014; U.S. Provisional Patent Application Ser. No. 62/037,801, entitled "Process and System for Making Cyclohexanone," and filed on Aug. 15, 2014; U.S. Provisional Patent Application Ser. No. 62/037,814, entitled "Process and System for Making Cyclohexanone," and filed on Aug. 15, 2014; U.S. Provisional Patent Application Ser. No. 62/037,824, entitled "Process and System for Making Cyclohexanone," and filed on Aug. 15, 2014; U.S. Provisional Patent Application Ser. No. 62/057,919, entitled "Process for Making Cyclohexanone," and filed on Sep. 30, 2014; U.S. Provisional Patent Application Ser. No. 62/057,947, entitled "Process for Making Cyclohexanone," and filed on Sep. 30, 2014; and U.S. Provisional Patent Application Ser. No. 62/057,980, entitled "Process for Making Cyclohexanone," and filed on Sep. 30, 2014, the contents of all of which are incorporated herein by reference in their entirety.

III.4 Post-Cleavage Treatment

The cleavage mixture exiting the cleavage reactor comprise, in addition to phenol, cyclohexanone, cyclohexylbenzene, acid catalyst if a liquid acid such as sulfuric acid is used in the cleavage step, and other contaminants Before the cleavage mixture is supplied to a first distillation column to separate the various components, the acid is removed or neutralized to prevent undesirable side reactions catalyzed by the acid in the first distillation column.

Preferably, a solid state basic material is used to neutralize the acid in the cleavage mixture. Doing so would reduce or eliminate the presence of acid species and/or S-containing components in media inside the first distillation column, avoid undesirable side reactions and byproducts formed as a result of contact with the acid species, reduce corrosion of the first distillation column caused by the acid species and the associated repair and premature replacement, and prevent undesirable side reactions and byproduct formation in subsequent steps.

Such basic materials useful for treatment according to any embodiment, advantageously in solid-phase under the operation conditions, can be selected from (i) oxides of alkali metals (e.g., Na), alkaline earth metals (e.g., Mg), and zinc; (ii) hydroxides of alkali metals (e.g., Na), alkaline earth metals (e.g., Mg), and zinc; (iii) carbonates of alkali metals (e.g., Na), alkaline earth metals (e.g., Mg), and zinc; (iv) bicarbonates of alkali metals (e.g., Na), alkaline earth metals (e.g., Mg), and zinc; (v) complexes of two or more of (i), (ii), (iii), and (iv); (vi) solid amines; (vii) ion-exchange resins; and (viii) mixtures and combinations of two or more of (i), (ii), (iii), (iv), (v), (vi), and (vii). Oxides, hydroxides, carbonates and bicarbonates of alkali and alkaline earth metals and zinc can react with acid to form salts thereof, which preferably, are also in solid-phase under the operation conditions. Preferably, an ion exchange resin is used. Such ion exchange resins preferably comprise groups on the surface thereof capable of adsorbing and/or binding with protons, $SO_3$, $HSO_4^-$, $H_2SO_4$, complexes of sulfuric acid, and the like. The ion exchange resin can comprise a strong and/or a weak base resin. Weak base resins primarily function as acid adsorbers. These resins are capable of adsorbing strong acids with a high capacity. Strong base anion resins can comprise quaternized amine-based products capable of adsorbing both strong and weak acids. Commercial examples of basic ion exchange resins useful in the present invention include but are not limited to: Amberlyst® A21 and Amberlyst® A26 basic ion exchange resins available from Dow Chemical Company. Amberlyst® A26 is an example of a strong base, type 1, anionic, macroreticular polymeric resin. According to Dow Chemical Company, the resin is based on crosslinked styrene divinylbenzene copolymer, containing quaternary ammonium groups. A26 is generally considered to be a stronger base resin than A21.

After treatment using a solid-phase base and/or ion exchange resin, both total acid concentration and acid precursor concentration (including concentration of S-containing components) in the feed supplied to the first distillation column can be exceedingly low (e.g., 50 ppm or less, such as less than or equal to 20, 15, 10, 5, or 1 ppm). Accordingly, the first distillation column can be operated at a high operation temperature, such as temperatures higher than the disassociation temperatures of complex materials formed between the acid catalyst used in the cleavage step, such as sulfuric acid, and the following organic amines: (i) pentane-1,5-diamine; (ii) 1-methylhexane-1,5-diamine; (iii) hexane-1,6-diamine; (iv) 2-methylpentane-1,5-diamine; (v) ethylene diamine; (vi) propylene diamine; (vii) diethylene triamine; and (viii) triethylene tetramine, without the concern of issues associated with acid produced from thermal dissociation thereof under such high operation temperature.

Additional detailed description of post-cleavage treatment of the cleavage mixture can be found in WO 2017/023430, the relevant portion of which is incorporated herein by reference in its entirety.

III.5 Separation and Purification

The neutralized cleavage reaction product can then be separated by methods such as distillation. In one example, in a first distillation column after the cleavage reactor, a heavies fraction (a lower effluent) comprising heavies (such as amine sulfuric acid complex, which can be regarded as an amine sulfate salt, if an organic amine is used to neutralize at least a portion of the sulfuric acid present in the cleavage reaction product before it is fed into the first distillation column) is obtained at the bottom of the column, a side fraction (equivalent to a middle effluent) comprising cyclohexylbenzene is obtained in the middle section, and an upper fraction (equivalent to an upper effluent) comprising cyclohexanone, phenol, methylcyclopentanone, 3-cyclohexenone and/or 2-cyclohexenone, and water is obtained.

The separated cyclohexylbenzene fraction can then be treated and/or purified before being delivered to the oxidation step. Since the cyclohexylbenzene separated from the cleavage product mixture may contain phenol and/or olefins such as cyclohexenylbenzenes, the material may be subjected to treatment with an aqueous composition comprising a base and/or a hydrogenation step as disclosed in, for example, WO 2011/100013A1, the entire contents of which are incorporated herein by reference.

In one example, the fraction comprising phenol, cyclohexanone, 3-cyclohexenone and/or 2-cyclohexenone, and water can be further separated by simple distillation to obtain an upper fraction comprising primarily cyclohexanone and methylcyclopentanone and a lower fraction comprising primarily phenol, and some cyclohexanone. Cyclohexanone cannot be completely separated from phenol without using an extractive solvent due to an azeotrope formed between these two. Thus, the upper fraction can be further distillated in a separate column to obtain a cyclohexanone product in the vicinity of the bottom and an impurity fraction in the vicinity of the top comprising primarily methylcyclopentanone, which can be further purified, if needed, and then used as a useful industrial material. Because 3-cyclohexenone cannot be completely separated from cyclohexanone by conventional distillation, the cyclohexanone product may need to be subject to a hydrogenation step to abate the 3-cyclohexenone to a desirable level. The lower fraction can be further separated by a step of extractive distillation using an extractive solvent (e.g., sulfolane, and glycols such as ethylene glycol, propylene glycol, diethylene glycol, triethylene glycol, and the like) described in, e.g., co-assigned, co-pending patent applications WO 2013/165656A1 and WO 2013/165659, the contents of which are incorporated herein by reference in their entirety. An upper fraction comprising cyclohexanone and a lower fraction comprising phenol and the extractive solvent can be obtained. In a subsequent distillation column, the lower fraction can then be separated to obtain an upper fraction comprising a phenol product and a lower fraction comprising the extractive solvent. The upper fraction rich in cyclohexanone, if containing 3-cyclohexenone, can be likewise subject to a hydrogenation step to abate the 3-cyclohexenone concentration to a desirable level, preferably combined together with other cyclohexanone-rich streams containing 3-cyclohexenone in need of abatement.

III.6 Separation and Hydrogenation Reaction

At least a portion, preferably the entirety, of the neutralized cleavage effluent (cleavage reaction product), may be separated and a phenol-containing fraction thereof can be provided as a feed mixture supplied to a hydrogenation zone, where at least a portion of the phenol is hydrogenated to form cyclohexanone. The phenol-containing fraction can contain cyclohexanone, 3-cyclohexenone and optionally 2-cyclohexenone. As discussed above, under the typical hydrogenation conditions adapted for phenol hydrogenation, 3-cyclohexenone and 2-cyclohexenone tend to convert at a much higher reaction rate than phenol, and if 3-cyclohexenone and 2-cyclohexenone are incorporated at a relatively low concentration, such as at most 5 wt %, a great majority, and even substantially all of 3-cyclohexenone and 2-cyclohexenone can be converted to cyclohexanone. Thus, the process may include providing a phenol-containing hydrogenation feed to a hydrogenation reaction zone, wherein the phenol-containing hydrogenation feed comprises the phenol-containing fraction from the aforementioned separation of a cleavage effluent. In any embodiment, the hydrogenation feed may further comprise one or more recycle streams or other streams comprising a higher weight % of either phenol or cyclohexanone, as compared to the phenol-containing stream drawn from separation. Thus, in any embodiment, the hydrogenation feed may have a weight ratio of phenol to cyclohexanone within the range of 0.15 to 4.0. In any embodiment, the weight ratio is within the range of 0.15 to 0.9 (e.g., where a cyclohexanone-containing stream is combined with the hydrogenation feed, and/or wherein the phenol-containing stream withdrawn from separation of the cleavage reaction product contains most or all of the cyclohexanone in the cleavage reaction product), whereas in others, it is within the range of 1.0 to 4.0, preferably 2.0 to 4.0.

A hydrogenation reaction zone may comprise any one or more hydrogenation reactors, which reactors may be arranged in series, in parallel, or in any combination thereof. For ease of illustration, many figures and their accompanying discussions in the ensuing description include only a single hydrogenation reactor, but it should be understood that any embodiment may employ multiple hydrogenation reactors arranged in series or in parallel in place of such hydrogenation reactors. Further, in embodiments employing multiple hydrogenation reactors (whether in series or in parallel), hydrogen supply may be staged across such multiple reactors, so that each reactor can receive hydrogen feed. A preferred hydrogenation reactor (any one or more of which may constitute a hydrogenation reaction zone) is a shell-and-tubes type hydrogenation reactor. Such a reactor may comprise one or more tubes in which hydrogenation catalyst is disposed, and through which hydrogenation reaction feed flows. The tube(s) are themselves disposed within a shell such that the shell carries temperature-control media (e.g., water, refrigerant, or another process stream) capable of absorbing heat from the hydrogenation reaction(s) taking place within the tubes. The fluid flowing through the shell and over the tube(s) may also or instead carry heat to the hydrogenation catalyst disposed within the tubes. For instance, the hydrogenation catalyst may periodically be regenerated by heating (discussed in more detail below), and such heating may be carried out in situ in the hydrogenation reactor by providing heat through a fluid flowing through the shell and over the tube(s).

The hydrogenation reaction zone includes a hydrogenation catalyst, in the presence of which various reactions take place. Preferably, each reactor in the hydrogenation reaction zone comprises a bed of hydrogenation catalyst (i.e., a hydrogenation catalyst bed) disposed therein.

The hydrogenation catalyst may comprise a hydrogenation metal performing a hydrogenation function supported on a support material. The hydrogenation metal can be, e.g., Fe, Co, Ni, Ru, Rh, Pd, Ag, Re, Os, Ir, and Pt, and mixtures and combinations of one or more thereof. Pd is a particularly preferred hydrogenation metal according to some embodiments. The concentration of the hydrogenation metal can be, e.g., in a range from 0.001 wt % to 7.5 wt % (such as 0.01 wt % to 5.0 wt %), based on the total weight of the catalyst. Preferably, the metal is present in its fully reduced metal state (e.g., $Pd^0$ as opposed to Pd oxide ($Pd^{+2}$ oxidation state)). The support material can be advantageously an inorganic material, such as oxides, glasses, ceramics, molecular sieves, and the like. For example, the support material can be activated carbon, $Al_2O_3$, $Ga_2O_3$, $SiO_2$, $GeO_2$, SnO, $SnO_2$, $TiO_2$, $ZrO_2$, $Sc_2O_3$, $Y_2O_3$, alkali metal oxides, alkaline earth metal oxides, and mixtures, combinations, complexes, and compounds thereof. Preferred supports include $Al_2O_3$ and/or activated carbon. Hydrogenation catalysts according to in any embodiment may further comprise an alkali or alkaline earth metal dopant (e.g., a sodium dopant) in amounts ranging from about 0.1 to about 3 wt %, such as about 0.5 to 1.5 wt %. Furthermore, without wishing to be bound by theory, it is believed that the preferred hydrogenation reactions occur quickly in the presence of the hydrogenation metal. Therefore, it is highly desirable that the hydrogenation metal is preferentially distributed in the outer rim of the catalyst particles, i.e., the concentration of the hydrogenation metal in the catalyst particle surface layer is higher than in the core thereof. Such rimmed catalyst can reduce the overall hydrogenation metal loading, reducing cost thereof, especially if the hydrogenation metal comprises a precious metal such as Pt, Pd, Ir, Rh, and the like. The low concentration of hydrogenation metal in the core of the catalyst particle also leads to a lower chance of hydrogenation of cyclohexanone, which may diffuse from the surface to the core of the catalyst particles, resulting in higher selectivity of cyclohexanone in the overall process.

It is believed that the catalyst surface can have different degrees of adsorption affinity to the different components in the reaction media such as phenol, cyclohexanone, cyclohexanol, 2-cyclohexenone, 3-cyclohexenone, cyclohexylbenzene, and bicyclohexane. It is highly desired that the catalyst surface has higher adsorption affinity to phenol, 2-cyclohexenone and 3-cyclohexenone than to cyclohexanone and cyclohexylbenzene. Such higher phenol, 2-cyclohexenone and 3-cyclohexenone adsorption affinity will give phenol competitive advantages in the reactions, resulting in higher selectivity to cyclohexanone, lower selectivity of cyclohexanol, and lower conversion of cyclohexylbenzene, which are all desired in a process designed for making cyclohexanone.

As noted, numerous reactions may take place in the hydrogenation reaction zone. The possibilities are generally complicated as compared to conventional phenol hydrogenation reactions by virtue of the presence of cyclohexanone and cyclohexylbenzene in the feed.

To further complicate matters, various impurities may be present in the hydrogenation feed (e.g., from one or more upstream processes in accordance with the hydroalkylation, oxidation, and cleavage reaction processes described previously). For instance, the hydrogenation feed may further comprise cyclohexanol and/or other oxygenated hydrocarbon compounds produced as byproducts of interactions between components in previously-described upstream processes, such as condensation reaction products.

Furthermore, certain light components, such as organic acids (e.g., formic acid, acetic acid, propanoic acid, linear, linear branched and cyclic carboxylic acids comprising 5, 6, 7, or 8 carbon atoms such as benzoic acid), N-containing compounds (e g, amines, imides, amides, $NO_2$-substituted organic compounds), and S-containing compounds (e.g., sulfides, sulfites, sulfates, sulfones, $SO_3$, $SO_2$) may be present in the hydrogenation feed. Such light components, if contained in the reaction mixture in the hydrogenation reactor and allowed to contact the hydrogenation metal under the hydrogenation reaction conditions, may poison the hydrogenation catalyst, leading to reduction of performance or premature failure of the catalyst. The aforementioned light components (organic acids, N-containing compounds, and S-containing compounds) are therefore also referred to as catalyst poison components. To avoid catalyst poisoning, it is highly desirable that the hydrogenation feed comprises such catalyst poison components at low concentrations (such as 0 to 5000 ppm by weight each, preferably 0 to 1000 ppm by weight each, such as 1 ppm by weight to 100 ppm by weight).

III.7 Pre-Hydrogenation Treatments

In view of the foregoing, in any embodiment include treating one or more of: (1) a hydrogen feed stream and (2) a hydrogenation feed stream comprising phenol, cyclohexanone, and cyclohexylbenzene supplied to a hydrogenation reaction zone, using one or more pre-hydrogenation treatments in order to, e.g., (i) remove impurities; (ii) suppress undesired side reactions; and/or (iii) improve catalyst life and/or selectivity to the desired cyclohexanone product, among other reasons. In other words, hydrogenation feed treatments discussed herein may be applied to a phenol-containing process stream at any point between (1) initial separation of the cleavage effluent into at least the phenol-containing stream and (2) provision of the phenol-containing process stream to a hydrogenation reaction zone. Such treatments need not be applied to a hydrogenation stream, but also or instead may be applied directly to a hydrogenation reaction zone itself (e.g., a compound provided as a pre-hydrogenation treatment may be supplied via one or more feed streams provided to the hydrogenation reaction zone separately from the hydrogenation feed stream).

Pre-hydrogenation treatment according to some embodiments includes passing a hydrogenation feed stream through one or more sorbents and/or one or more additional distillation columns (referred to herein as "posterior sorbents" and "posterior distillation columns," indicating downstream relationship relative to the separation of cleavage effluent or other stream into at least a phenol-containing stream). Such posterior sorbent and/or posterior distillation treatment may be instead of or in addition to the treatment of cleavage reaction product to remove catalyst poison components such as S-containing components prior to separation of the cleavage reaction product, discussed above.

Pre-hydrogenation treatment according to other embodiments may also, or instead, include the addition of basic chemical agents to the hydrogenation feed stream in order to condition the hydrogenation catalyst (e.g., by tuning the acidity of the catalyst). Suitable basic chemical agents include one or more bases selected from the group consisting of amines, soluble inorganic bases, and mixtures thereof. Such chemical agents are added to the hydrogenation feed as solutions, or are dissolved into the feed (as opposed to passing the feed through solid-phase basic ion exchange resin, per the previous description). Alternatively or in addition, such chemical agents may be provided directly to the hydrogenation reaction zone separately from the hydrogenation feed. Preferred examples of amine chemical agents include alkylamines, such as the primary, secondary, and tertiary alkylamines, cyclic amines, etc., regardless of carbon type or chain length (e.g., methylamine, monoethanolamine, dimethylamine as particular examples). Preferred examples of inorganic base chemical agents include alkali metal and alkaline earth metal compounds (e.g., NaOH and $Na_2CO_3$ in particular). Without wishing to be bound by theory, it is believed that such agents may condition the acidity inherent in hydrogenation catalysts according to some embodiments. For instance, various hydrogenation catalyst supports (e.g., $Al_2O_3$, activated carbon) contain varying degrees of acidic sites; addition of a basic chemical agent to a hydrogenation feed may result in such basic chemical agents reacting with the catalyst's acidic sites, so as to reduce the acidity of the catalyst. This may improve catalyst life and/or phenol conversion rate, and/or cyclohexanone selectivity. Furthermore, addition of such basic chemical agents (e.g., $Na_2CO_3$) may lower the selectivity to cyclohexanol and may inhibit the undesired hydrogenation of cyclohexylbenzene present in the hydrogenation feed. Such chemical agents are preferably supplied to the hydrogenation feed stream and/or hydrogenation reaction zone in amounts ranging from about 0.01 to 5 wt %, preferably 0.01 to 0.1 wt %, most preferably about 0.03 to 0.07 wt %, on the basis of hydrogenation feed (exclusive of hydrogen and any inert fluids that may be provided to the hydrogenation reaction zone with the hydrogenation feed).

Pre-hydrogenation treatment according to yet further embodiments also, or instead, includes providing water to one or more of a hydrogenation feed stream or the hydrogenation reaction zone. Water may be added in amounts ranging from about 0.1 wt % to 20 wt %, on the basis of hydrogenation feed provided to the hydrogenation reaction zone (exclusive of hydrogen and any inert fluids provided to the hydrogenation reaction zone). Water may be added in relatively low amounts in any embodiment (e.g., preferably 0.1 wt % to 3 wt %, such as 1 wt % to 3 wt %), or is added in relatively high amounts (e.g., preferably 5 wt % to 20 wt %, such as 6 wt % to 15 wt %). In any embodiment, where water is added in relatively high amounts, the amount of water added is based upon the phenol present in the hydrogenation feed. For instance, phenol may be added at a water to phenol weight ratio of at least 0.10, more preferably at least 0.12, such as at least 0.15. Addition of water according to some embodiments may serve multiple useful purposes. For instance, it may suppress various undesired side reactions. In particular, it may suppress the undesired side reaction of hydrogenation of cyclohexylbenzene. It is hypothesized that a small amount of water may form a hydrophilic layer on the hydrogenation catalyst surface, preventing the diffusion of cyclohexylbenzene to the catalyst surface (and thereby inhibiting the catalyzed hydrogenation of cyclohexylbenzene), while permitting the more polar phenol compounds to continue to diffuse to the catalyst, where the phenol is hydrogenated. Water may also suppress the formation of condensation products from components in the hydrogenation feed (e.g., aldols and the like). Since water is formed as a product of such equilibrium-driven reactions, the presence of water may suppress the occurrence of such reactions. This is advantageous insofar as the non-water condensation products may adsorb to the hydrogenation catalyst, plugging sites that could otherwise be used by phenol to be hydrogenated, and thereby significantly decreasing the conversion of phenol over the hydrogenation catalyst as time passes.

It should also be noted that a chemical agent (e.g., $Na_2CO_3$) may be supplied to the hydrogenation feed stream and/or the hydrogenation reaction zone as an aqueous solution. The aqueous solution may be provided in amounts sufficient to provide the aforementioned amounts of water to the hydrogenation reaction zone, thereby effectively combining two treatment methods.

Pre-hydrogenation treatment according to further embodiments includes diluting a hydrogen feed stream to the hydrogenation reaction zone with an inert fluid, such as nitrogen, methane, steam, or any other substance capable of controlling the hydrogenation reaction selectivity by reducing or diminishing the hydrogen partial pressure in the reaction zone. Such hydrogen partial pressure will vary with reactor operating pressure. A convenient way to represent the hydrogen partial pressure effect on the hydrogenation process is to operate at a desired hydrogen to phenol molar ratio, which may range from about 0.1 to 6.0 (preferably about 2.0 to about 4.0) moles hydrogen to moles phenol fed to the hydrogenation reaction zone.

Yet further embodiments include temporarily introducing one or more hydrogenation catalyst inhibitors to the hydrogenation feed and/or the hydrogenation reaction zone (that is, continuously introducing the catalyst inhibitor for only a limited period of time that is shorter than the period of time during which hydrogenation feed is continuously introduced to the hydrogenation reaction zone). A "catalyst inhibitor" as used herein should be understood as any compound that is capable of temporarily and reversibly suppressing the activity of a hydrogenation catalyst (e.g., by reversibly adsorbing to active hydrogenation metal sites on the catalyst). A catalyst inhibitor is distinct from a catalyst poison component insofar as the catalyst inhibitor's effect may be readily controlled so as to be temporary and reversible during normal process conditions simply by ceasing the supply of the catalyst inhibitor. For instance, the catalyst inhibitor CO may adsorb onto active metal sites on the hydrogenation catalyst, but be readily desorbed by other components of the hydrogenation feed and/or hydrogen feed. Thus, once continuous flow of CO to the hydrogenation reaction zone stops, the remaining CO will desorb, restoring catalyst activity. Such a temporary effect is advantageous during start-up of a process with fresh catalyst (e.g., freshly-reduced, activated catalyst), which may be hyper-active. Such highly active catalyst may promote a higher-than-desired phenol hydrogenation rate, which could lead to excessive, difficult to control, heat release. Excessively high catalyst activity may also cause formation of undesired byproducts (e.g., via hydrogenation of cyclohexanone to cyclohexanol).

Accordingly, processes according to some embodiments include continuously introducing hydrogen, a hydrogenation feed, and a catalyst inhibitor to the hydrogenation reaction zone (e.g., as a separate feed or as part of the hydrogenation and/or hydrogen feed) during a first time period so as to inhibit activity of a hydrogenation catalyst disposed within the hydrogenation reaction zone (e.g., by adsorbing onto one or more active hydrogenation metal sites on the catalyst), and subsequently ceasing the introduction of the catalyst inhibitor to the hydrogenation reaction zone so as to stop the inhibition of hydrogenation catalyst activity (e.g., by allowing the catalyst inhibitor to desorb from the one or more active hydrogenation metal sites on the catalyst), and thereafter continuing to introduce the hydrogen and the hydrogenation feed into the hydrogenation reaction zone during a second time period subsequent to the first time period. Suitable catalyst inhibitors include CO, and, potentially, $H_2S$ at low levels. Preferably, the catalyst inhibitor is CO. Catalyst inhibitor is fed as a vapor, in a range from 0 vol % to 1 vol % on the basis of hydrogen fed to the hydrogenation reaction zone, preferably 1 to 100 ppm by volume (on the basis of hydrogen fed to the hydrogenation reaction zone).

III.8 Catalyst Regeneration/Rejuvenation

Notwithstanding the use of the foregoing pre-hydrogenation treatments, hydrogenation catalyst activity may still decrease as normal operation of a hydrogenation reaction zone progresses over time. Accordingly, some embodiments provide for methods for regenerating and/or rejuvenating the hydrogenation catalyst disposed within one or more hydrogenation reactors of a hydrogenation reaction zone.

Methods according to some such embodiments advantageously include on-stream catalyst regeneration or rejuvenation (i.e., regeneration or rejuvenation that takes place while hydrogenation feed is provided to the hydrogenation reaction zone, so as to allow for the desired phenol hydrogenation while the catalyst is being regenerated). A particular example of such a process is mixed-phase operation of the hydrogenation reaction, meaning that the hydrogenation reaction medium (comprising unreacted hydrogenation feed and any products and byproducts formed within the reaction zone) contacting the hydrogenation catalyst within the hydrogenation reaction zone is in mixed liquid and vapor phase. It is believed that when at least a portion of the hydrogenation feed contacting the hydrogenation catalyst is maintained in liquid phase, the liquid phase portion of the feed serves as a liquid wash, which removes impurities (e.g., hydrocarbon and/or oxygenate impurities, catalyst poisons, and the like) that have adsorbed or absorbed onto the hydrogenation catalyst (either on active metal sites or on the support, so as to block phenol's access to active metal sites). The impurities may be removed by physical effects and/or chemical interaction with the partially liquid-phase flow (e.g., the liquid may displace the impurities, and/or the impurities may be at least partially soluble in the liquid-phase reaction medium contacting the catalyst bed, such that the impurities are dissolved within the passing liquid). In order to provide this washing effect, it is preferred that liquid hold-up and/or liquid flux through a bed of hydrogenation catalyst be maintained at or above certain levels. Thus, during mixed-phase operation according to some embodiments, liquid holdup in a hydrogenation reaction zone (e.g., a hydrogenation reactor) should be maintained at greater than or equal to 1 vol %, based upon the available void volume in the hydrogenation catalyst bed within the hydrogenation reaction zone. Preferably, liquid mass flux through the hydrogenation catalyst bed is at least 2 $kg/m^2s$. Where the hydrogenation reaction zone comprises multiple hydrogenation catalyst beds (e.g., where the hydrogenation reaction zone comprises multiple hydrogenation reactors, and/or comprises one or more shell-and-tube hydrogenation reactors with multiple tubes), the liquid mass flux through each catalyst bed is at least 2 $kg/m^2s$. Liquid mass flux is determined based upon the cross-sectional area through which the liquid passes (e.g., the cross-sectional area of the catalyst bed, or, where the catalyst bed is disposed within a hydrogenation reactor, the cross-sectional area of the reactor).

Generally, mixed-phase operation is obtained by adjusting and/or maintaining hydrogenation reaction conditions (particularly temperature and/or pressure). It is well within the ability of an ordinarily skilled artisan to determine suitable combinations of temperature and pressure for mixed-phase operation with minimal experimentation. In particular, an ordinarily skilled artisan will recognize that temperature and pressure are co-dependent (that is, the pressure at which mixed-phase conditions exist depends in part upon the temperature in the hydrogenation reaction zone, and vice-versa). Thus, numerous different combinations of temperature and pressure to arrive at mixed-phase conditions are possible. In general, for a given temperature that is held constant, higher pressure will be needed to move from vapor to mixed-phase. And, for a given pressure that is held constant, lower temperature will be needed to move from vapor to mixed-phase. And, of course, a combination of higher pressure and lower temperature may also be used to move reaction conditions from vapor phase to mixed-phase.

In general, mixed-phase conditions will exist with temperature within the range of 25° C. to 250° C., and pressure within the range of 0 kPa (gauge) to 2000 kPa (gauge), while vapor phase operation will include temperature within the range from 100° C. to 300° C. and pressure within the range from 0 kPa (gauge) to 2000 kPa (gauge). For temperatures within the lower end of a given range, pressure may correspondingly be in the lower end of the range. Conversely, when temperature is at the higher end of the range, it will be necessary for pressure to be at the higher end of the range so as to ensure mixed-phase operation. For example, for pressures of 175 kPa (gauge) or less, temperature in the range of 150 to 200° C. results in vapor-phase operation. But at pressures of around 800 kPa (gauge), temperature may range from 100° C. to 200° C. to enable mixed-phase operation. As another example, vapor phase conditions may include about 70 kPa (gauge) and 165° C. to 180° C., while mixed-phase conditions at 70 kPa (gauge) would exist at 120° C. In some particular embodiments, mixed-phase conditions are maintained by maintaining temperature within the range of 100° C. to 200° C., and maintaining pressure at 800 kPa (gauge) or less, while adjusting the conditions to simultaneously maintain mixed-phase operation and also maintaining an acceptable hydrogenation reaction rate.

Mixed-phase operation as described above may be maintained as the normal operating condition of the hydrogenation reaction. Thus, methods according to some embodiments include continuously providing hydrogen and hydrogenation feed comprising phenol, cyclohexanone, and cyclohexylbenzene to a hydrogenation reaction zone in which a hydrogenation catalyst bed is disposed, thereby maintaining a reaction medium flowing through the hydrogenation catalyst bed within the hydrogenation reaction zone; and maintaining temperature and pressure in the hydrogenation reaction zone such that the reaction medium flowing through the hydrogenation catalyst bed remains in mixed liquid and vapor phase.

In yet other embodiments, mixed-phase operation may be a temporary departure from standard operating conditions (either vapor or liquid phase operations, preferably a departure from standard vapor-phase operating conditions). In particular embodiments, the hydrogenation reaction is normally operated in vapor phase, with one or more temporary departures to operation in the mixed liquid- and vapor-phase so as to achieve a liquid washing effect. Thus, methods according to some embodiments include (a) during a first period of time, flowing (i) hydrogen and (ii) a vapor-phase hydrogenation feed comprising phenol, cyclohexanone, and cyclohexylbenzene through a hydrogenation catalyst bed so as to hydrogenate at least a portion of the phenol in the vapor-phase hydrogenation feed to cyclohexanone, and further so as to form one or more hydrocarbon and/or oxygenate impurities that adsorb or absorb onto at least a portion of the hydrogenation catalyst bed; and (b) during a second period of time subsequent to the first period of time, flowing (i) hydrogen and (ii) a mixed liquid- and vapor-phase hydrogenation feed comprising phenol, cyclohexanone, and cyclohexylbenzene through the hydrogenation catalyst bed so as to hydrogenate at least a portion of the phenol in the mixed liquid- and vapor-phase hydrogenation feed to cyclohexanone, and further so as to remove at least a portion of the one or more hydrocarbon and/or oxygenate impurities from the hydrogenation catalyst bed.

Methods according to yet further embodiments of temporary mixed-phase operation include: (a) during a first period of time, continuously providing hydrogen and a hydrogenation feed to a hydrogenation reaction zone in which hydrogenation catalyst is disposed, thereby maintaining a reaction medium flowing through the hydrogenation catalyst bed within the hydrogenation reaction zone, while maintaining initial temperature and initial pressure conditions within the hydrogenation reaction zone such that the reaction medium is entirely in vapor phase during the first period of time; (b) adjusting the initial temperature conditions, the initial pressure conditions, or both, within the hydrogenation reaction zone to obtain liquid washing temperature and pressure conditions within the hydrogenation reaction zone, such that the reaction medium is in mixed liquid and vapor phase after the adjusting; and (c) during a second period of time subsequent to the first period of time, maintaining the liquid washing temperature and pressure conditions within the hydrogenation reaction zone while continuously providing the hydrogen and the hydrogenation feed to the hydrogenation reaction zone, thereby maintaining the reaction medium flowing through the hydrogenation catalyst bed in mixed liquid and vapor phase.

In yet other embodiments, hydrogenation catalyst regeneration and/or rejuvenation may also or instead be carried out off-stream (that is, in the absence of the provision of hydrogenation feed to a hydrogenation reactor within the hydrogenation reaction zone). Preferably, in such embodiments, the hydrogenation reaction zone comprises multiple hydrogenation reactors configured such that, while one or more of the reactors are taken off-line (e.g., provision of hydrogenation feed to such reactors is halted), the remainder of the reactors remain in normal operation (e.g., hydrogenation feed and hydrogen continue to be supplied to the remainder of the reactors such that phenol hydrogenation continues to take place in the remainder of the reactors). This configuration may be effected by any suitable means, such as parallel operation of the multiple hydrogenation reactors of such hydrogenation reaction zones, and/or by the use of a manifold to enable a hydrogenation feed to be selectively provided to any one or more of a plurality of hydrogenation reactors within the hydrogenation reaction zone.

Once taken out of service, a hydrogenation reactor can be subjected to a purging fluid that is preferably inert when contacted with the hydrogenation catalyst (e.g., any one or more of nitrogen, methane, steam, or a combination thereof). The purging fluid removes byproducts and other compounds adsorbed, absorbed, or otherwise trapped within the porous structure of the hydrogenation catalyst bed disposed within that reactor. Also or instead, the hydrogenation catalyst may be regenerated by conducting a controlled oxidative burn with dilute air so as to combust hydrocarbons and/or oxygenates trapped within the hydrogenation catalyst as CO, $CO_2$, and $H_2O$. Such dilute air may be generated by mixing air with diluent gases known to those skilled in the art. The catalyst regenerated according to such embodiments is then purged to remove residual oxygen, and is subsequently reduced by flowing a dilute hydrogen stream at process conditions sufficient to attain complete reduction of the catalyst's active hydrogenation metals such as Pd (that is, such metals are converted from their oxide states to their fully reduced metal states). The reactor may then be placed back in service.

Preferably, once a reactor is placed in service in a hydrogenation reaction zone comprising multiple hydrogenation reactors in series, the newly in-service reactor is placed in the tail-end of the multiple series reactors. That is, the hydrogenation reactor subjected to the out-of-service rejuvenation/regeneration procedure just described (i.e., the regenerated reactor) is preferably returned to service by providing the effluent of the most down-stream hydrogenation reactor of the hydrogenation reaction zone to the regenerated reactor.

IV. Cyclohexanone-Containing Products

In any embodiment, the methods and/or systems described herein can be used to make cyclohexanone-containing products that are depleted in 3-cyclohexenone. Such products can comprise, based on its total weight, at least 10 wt % of cyclohexanone; 0 to 90 wt % of cyclohexanol; and 0.01 to 20 ppm of 3-cyclohexenone.

Preferably, the cyclohexanone-containing product is a high-purity cyclohexanone product comprising at least 99 wt % cyclohexanone, based on the total weight of the cyclohexanone-containing product. More preferably, the high-purity cyclohexanone product comprises at least 99.90 wt %, 99.94 wt %, 99.95 wt %, or even 99.99 wt % cyclohexanone.

The cyclohexanone-containing product can be a KA oil product comprising cyclohexanol at any concentration in the range from 5 to 90 wt %, such as from 10 to 80 wt %, from 20 to 70 wt %, from 30 to 60 wt %, or from 40 to 50 wt %.

The cyclohexanone-containing product can comprise 3-cyclohexenone at a concentration in the range from f1 to f2 ppm, based on the total weight of the cyclohexanone-containing product, where f1 and f2 can be, independently, 0.01, 0.05, 0.1, 0.05, 1, 2, 3, 4, 5, 6, 7, 8, 9, 10, as long as f1<f2.

The cyclohexanone-containing product can comprise 2-cyclohexenone at a concentration in the range from g1 to g2 ppm, based on the total weight of the cyclohexanone-containing product, where g1 and g2 can be, independently, 0.01, 0.05, 0.1, 0.05, 1, 2, 3, 4, 5, 6, 7, 8, 9, 10, as long as g1<g2.

The cyclohexanone-containing product may further comprise one or more additional cyclohexanone impurities selected from the following compounds: benzene, cyclohexene, pentanal, cyclopentanol, cyclohexanol, and phenol. As used herein, a "cyclohexanone impurity" is any compound other than cyclohexanone or water, which is typically acceptable in commercially available cyclohexanone-containing products in small amounts. Water is desirably present in the cyclohexanone composition in amounts of 0.15 wt % or less, such as 0.1 wt % or less, or 0.05 wt % or less, based on total weight of the cyclohexanone-containing product. Preferably, the total amount of cyclohexanone impurities is 500 ppm by weight or less, more preferably 200 ppm by weight or less, most preferably 150 ppm by weight or less, or even 100 ppm by weight or less, each ppm by weight being based upon the total weight of the cyclohexanone-containing product.

The cyclohexanone-containing product may comprise any one or more, two or more, three or more, or four or more of such cyclohexanone impurities. In particular embodiments, the cyclohexanone-containing product comprises one or both of pentanal and cyclopentanol each at concentration of 200 ppm by weight or less, preferably 100 ppm by weight or less. Compositions of such embodiments may also or instead comprise one or both of cyclohexene and cyclohexanol each at concentration of 200 ppm by weight or less, preferably 100 ppm by weight or less.

In any embodiment, the cyclohexanone-containing product may consist of cyclohexanone, 2-cyclohexenone at the above described concentrations, 3-cyclohexenone at the above described concentration, 0.15 wt % or less (preferably 0.1 wt % or less, most preferably 0.05 wt % or less) water, and 500 ppm by weight or less (preferably 200 ppm by weight or less, most preferably 100 ppm by weight or less) of one or more cyclohexanone impurities. The cyclohexanone impurities in such embodiments are preferably selected from the group consisting of: benzene, cyclohexene, pentanal, cyclopentanol, cyclohexanol, 2-cyclohexenone, 3-cyclohexenone, and phenol. In any embodiment, the cyclohexanone impurities are selected from the group consisting of: cyclohexene, pentanal, cyclopentanol, and cyclohexanol. Such compositions may consist of any one, two, three, or four of the foregoing impurities. In particular embodiments, the impurities consist of cyclohexene, pentanal, cyclopentanol, and cyclohexanol. In yet further particular embodiments, the impurities consist of (i) cyclohexene, (ii) cyclopentanol or pentanal, and (iii) cyclohexanol.

With respect to each aforementioned cyclohexanone impurity in the cyclohexanone-containing products:

Benzene may be present in an amount ranging from 0 to 20 ppm by weight. For instance, benzene may be present at 0 ppm by weight to 5 ppm by weight, preferably 0 ppm by weight to 2.5 ppm by weight.

Cyclohexene may be present in an amount ranging from 0 to 20 ppm by weight. For instance, cyclohexene may be present at 0 ppm by weight to 15 ppm by weight, such as 2.5 ppm by weight to 15, or 5 ppm by weight to 10 ppm by weight.

Pentanal may be present in an amount ranging from 0 to 200 ppm by weight. For instance, pentanal may be present at 0 ppm by weight to 100 ppm by weight, such as 1 ppm by weight to 80 ppm by weight, potentially 3 ppm by weight to 60 ppm by weight.

Total lights (including benzene, cyclohexene, pentanal, cyclopentanone, and pentanal) may be preferably present in an amount ranging from 10 to 2000 ppm by weight, more preferably from 10 to 1000 ppm by weight, still more preferably 20 to 500 ppm by weight, still more preferably 20 to 400 ppm by weight.

Cyclopentanol may be present in an amount ranging from 0 to 80 ppm by weight. For instance, cyclopentanol may be present at 10 ppm by weight to 50 ppm by weight, such as 15 to 40 ppm by weight, or 20 to 35 ppm by weight.

Cyclohexanol may be present in an amount ranging from 0 to 1000 ppm by weight. For instance, cyclohexanol may be present at 0 ppm by weight to 800 ppm by weight, such as 10 ppm by weight to 600 ppm by weight, for instance 50 ppm by weight to 500 ppm by weight, or 100 ppm by weight to 400 ppm by weight.

In any embodiment, any one or more of these cyclohexanone impurities may have been generated in situ during a process for making cyclohexanone (i.e., they were not added from an external source). For instance, any one or more of the cyclohexanone impurities may have been formed during the phenol hydrogenation reaction. This is particularly likely for cyclohexanone impurities such as cyclohexanol, cyclohexene, 2-cyclohexenone, 3-cyclohexenone, and water. Additionally, any trace amount of unreacted phenol left over from the hydrogenation reaction may remain as a cyclohexanone impurity. Furthermore, in any embodiment, at least a portion of the cyclohexene may have been produced at least in part during distillation or other treatment of all or part of the phenol hydrogenation reaction effluent.

Further, in any embodiment, all or at least part of the pentanal and/or cyclopentanol may be formed either before or after (i.e., upstream or downstream of, respectively) hydrogenation of the hydrogenation feed comprising cyclohexanone and phenol.

The cyclohexanone-containing product produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used, for example, to produce phenolic resins, bisphenol A, caprolactam, adipic acid, and/or plasticizers.

V. Composition of Matter Comprising Cyclohexylbenzene, Phenol, Cyclohexanone, and 3-Cyclohexenone Another aspect of the present disclosure is a composition of matter comprising 20 to 70 wt % of cyclohexylbenzene; 5 to 40 wt % of phenol; 5 to 40 wt % of cyclohexanone; and 50 ppm to 5 wt % of 3-cyclohexenone. This composition of matter can be desirably produced from the CHB-route, as a mixture obtainable from the cleavage reactor, with or without addition post-cleavage treatment as described above. This composition of matter can be advantageously used as the feed mixture for producing cyclohexanone-containing products depleted in 2-cyclohexenone and 3-cyclohexenone as described above.

Thus, the composition of matter can comprise 3-cyclohexenone at a concentration in the range from h1 to h2 ppm by weight, based on the total weight of the composition, where h1 and h2 can be, independently, 50, 80, 100, 200, 400, 500, 600, 800, 1000, 2000, 4000, 5000, 6000, 8000, $1\times10^4$, $2\times10^4$, $4\times10^4$, $5\times10^4$, $6\times10^4$, $8\times10^4$, $1\times10^5$, $2\times10^5$, $4\times10^5$, $5\times10^5$, $6\times10^5$, $8\times10^5$, $1\times10^6$, $2\times10^6$, $4\times10^6$, $5\times10^6$, as long as h1<h2. Preferably h1=50, h2=2000. More preferably h1=100, h2=1000.

The composition of matter can further comprise 2-cyclohexenone at a concentration in the range from j1 to j2 ppm by weight, based on the total weight of the composition, where j1 and j2 can be, independently, 50, 80, 100, 200, 400, 500, 600, 800, 1000, 2000, 4000, 5000, 6000, 8000, $1\times10^4$, $2\times10^4$, $4\times10^4$, $5\times10^4$, $6\times10^4$, $8\times10^4$, $1\times10^5$, $2\times10^5$, $4\times10^5$, $5\times10^5$, $6\times10^5$, $8\times10^5$, $1\times10^6$, $2\times10^6$, $4\times10^6$, $5\times10^6$, as long as j1<j2. Preferably j1=50, j2=2000. More preferably j1=100, j2=1000.

Thus, the composition of matter can comprise cyclohexylbenzene at a concentration in the range from k1 to k2 ppm by weight, based on the total weight of the composition, where k1 and k2 can be, independently, 20, 25, 30, 35, 40, 45, 50, 55, 60, 65, or 70, as long as k1<k2. Preferably k1=30, k2=65. More preferably k1=40, k2=60.

Thus, the composition of matter can comprise cyclohexanone at a concentration in the range from m1 to m2 ppm by weight, based on the total weight of the composition, where m1 and m2 can be, independently, 5, 10, 15, 20, 25, 30, 35, or 40, as long as m1<m2. Preferably m1=10, m2=35. More preferably m1=15, m2=30.

Thus, the composition of matter can comprise phenol at a concentration in the range from n1 to n2 ppm by weight, based on the total weight of the composition, where n1 and n2 can be, independently, 5, 10, 15, 20, 25, 30, 35, or 40, as long as n1<n2. Preferably n1=10, n2=35. More preferably n1=15, n2=30.

The present invention is further illustrated by the following non-limiting examples.

EXAMPLES

Examples of the separation and hydrogenation processes and/or systems according to some particular embodiments are illustrated in the attached drawings and described in detail below. It should be understood that processes and/or systems shown in the schematic, not-to-scale drawings are only for the purpose of illustrating the general material flows and general operating principles of particular embodiments in accordance with these illustrations. To simplify illustration and description, some routine components, such as pumps, valves, reboilers, pressure regulators, heat exchangers, recycling loops, condensers, separation drums, sensors, rectifiers, fillers, distributors, stirrers, motors, and the like, are not shown in the drawings or described herein. One having ordinary skill in the art, in light of the teachings herein, can add those components where appropriate. While the material flow direction in all hydrogenation reactors illustrated in the examples are from top to bottom, it is also possible to run streams from bottom to top in these reactors.

For Examples 2-5 below, exemplary but non-limiting first feed mixture (203, 303, 403, and 503, respectively) can desirably comprise: 20 to 70 (preferably 40 to 60) wt % of cyclohexylbenzene, 5 to 40 (preferably 15 to 30) wt % of phenol, 5 to 40 (preferably 15 to 30) wt % of cyclohexanone, and 0 to 20 (preferably 0 to 10) wt % of all other components combined (e.g., water, light acids, and the like) including about 30 ppm by weight to 1 wt % (preferably 50 to 5000 ppm by weight, more preferably 50 to 1000 ppm by weight) of 3-cyclohexenone and/or 2-cyclohexenone.

Example 1

A spinning band distillation ("SBD") was performed for a feed mixture consisting of 97 wt % cyclohexanone, 1 wt % cyclohexanol, 1 wt % 3-cyclohexenone, and 1 wt % 2-cyclohexenone, using an SBD instrument (model M690) available from B/R Instruments, which has an address at 9119 Centreville Road Easton, Md. 21601 USA. The SBD instrument included a stainless steel band set to 2000 rpm, which gave 15 stages of separation. The pressure was 78 mm Hg (10 kPa absolute pressure) and the pot temperature was 91° C. The reflux ratio was 30:1. A total of four fractions were taken from the distillation operation, labelled Fraction Nos. 1 to 4, respectively. Fraction No. 5 corresponds to the residual in the pot after all four fractions were taken. The starting feed mixture was labelled Fraction No. 0. Each fraction was measured for the concentrations of the four compounds. Concentration data of cyclohexanol, 2-cyclohexenone, and 3-cyclohexenone are reported in FIG. 1. As can be seen from FIG. 1, concentrations of 3-cyclohexenone in all Fraction Nos. 0, 1, 2, 3, 4, and 5 are substantially the same, and remain very close to the beginning concentration in the feed mixture of about 1 wt %. Based on these results, cyclohexanone and 3-cyclohexenone cannot be separated by distillation and have a relative volatility that is very close to 1. On the other hand, with respect to 2-cyclohexenone, its concentration increased gradually from Fraction No. 0 to Fraction Nos. 1, 2, 3, 4, and eventually reached the highest in Fraction No. 5, which is significantly higher than its concentration in the initial feed mixture. As such, 2-cyclohexenone can be separated from cyclohexanone by distillation.

Example 2

(Comparative)

Figure 2:
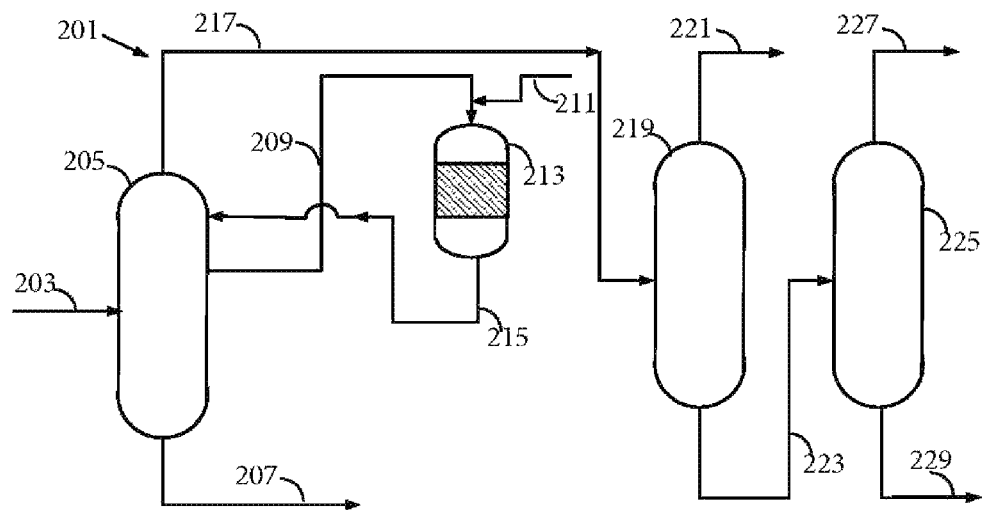
FIG. 2 is a schematic diagram showing a comparative process/system including a primary fractionator, a phenol hydrogenation reactor, and additional distillation columns, resulting in high concentration of 3-cyclohexenone in the cyclohexanone product.

FIG. 2 schematically illustrates a process/system 201 operating to produce cyclohexanone from a first feed mixture comprising cyclohexylbenzene, phenol, cyclohexanone, water, light acids, and 3-cyclohexenone. The first feed mixture stream 203 is fed into a first distillation column (also known as the primary fractionator in the present disclosure) 205 at a first feed mixture feeding location, where a lower effluent stream 207 (withdrawn preferably in the vicinity of the bottom of column 205) comprising cyclohexylbenzene and other optional heavy components is produced. Stream 207 can be further separated to obtain a substantially pure stream of cyclohexylbenzene, which can be recycled to an upstream oxidation reactor (not shown) where cyclohexylbenzene is oxidized to form cyclohexylbenzene hydroperoxide. From column 205, a middle effluent 209 is drawn at a middle effluent location above the first feed mixture location, but below the top of column 205. Stream 209, comprising cyclohexanone, phenol, cyclohexanol, 3-cyclohexenone, optionally 2-cyclohexenone, optionally bicyclohexane, and optionally cyclohexylbenzene, is then fed into a hydrogenation reactor 213 together with a stream of hydrogen 211. In the presence of a bed of hydrogenation catalyst installed inside reactor 213, 2-cyclohexenone, 3-cyclohexenone, and phenol undergo hydrogenation reactions to form cyclohexanone, cyclohexanone undergoes hydrogenation to form cyclohexanol, and the optional cyclohexylbenzene, if present, undergoes hydrogenation to form bicyclohexane. Hydrogenation of 2-cyclohexenone and 3-cyclohexenone are believed to be much faster than phenol hydrogenation under typical phenol hydrogenation conditions in the presence of the phenol hydrogenation catalyst. As such, the hydrogenation reactor effluent (also known as hydrogenated mixture) 215 comprises cyclohexanone and cyclohexanol at higher concentrations than stream 209, phenol at a reduced concentration than stream 209, and optional cyclohexylbenzene and bicyclohexane, and is substantially free of 2-cyclohexenone and 3-cyclohexenone. Stream 215 is recycled back to the first distillation column 205 at a first recycle stream location no more than 5 theoretical stages above the first middle effluent location. Above the first recycle stream location, a first upper effluent 217 is produced (preferably at a location in the vicinity of the top of column 205). Stream 217 comprises cyclohexanone, cyclohexanol, water, hydrogen, and other light components such as light acids and is substantially free of phenol. Stream 217 is then supplied to a second distillation column 219, where it is separated to obtain a light component-rich upper effluent stream 221 comprising water, hydrogen, and light acids, and a cyclohexanone-rich lower effluent stream 223 comprising cyclohexanone and cyclohexanol. Stream 223 is then fed into a third distillation column 225, where it is separated into a cyclohexanone upper effluent stream 227 and a lower effluent stream 229. Stream 227 can comprise cyclohexanone at a purity of higher than 90 wt %, preferably higher than 95 wt %, more preferably higher than 99 wt %. Stream 229 can comprise cyclohexanol at any concentration depending on the degree of separation in the third distillation column, but preferably in the range from 30 to 90 wt %, more preferably from 40 to 60 wt %. Streams 227 and 229 can be delivered to product storage and used for downstream applications such as productions of caprolactam, adipic acid, and the like.

As the results in Example 1 demonstrated, conventional distillation cannot completely separate a mixture of cyclohexanone and 3-cyclohexenone. The concentration of 3-cyclohexenone in the mixture at the first middle effluent location is substantial. While some of the material in recycle stream 215 travels downward to absorb a portion of the 3-cyclohexenone traveling upward from the first middle effluent location, the short distance of no more than 5 stages between the first middle effluent location and the recycle location is insufficient to suppress substantially all 3-cyclohexenone from reaching above the recycle location. Thus, the process of FIG. 2 is highly likely to result in the presence of 3-cyclohexenone in the first upper effluent stream 217, and eventually in streams 223, 227, and 229. Such likelihood is even higher when phenol conversion in the hydrogenation reactor 213 is high and the total quantity of liquid recycled to column 201 via stream 215 is therefore small.

A computer-based steady state process simulation was conducted for the process of 201 using Schneider Electric Software SimSci Pro/II (available from Schneider Electric Software having an address at 26561 Rancho Parkway, South Lake Forest, Calif. 92630, U.S.A.) to quantify the amount of 3-cyclohexenone in the product. 3-cyclohexenone conversion to cyclohexanone in phenol hydrogenation was assumed to be 100%. Phenol conversion was assumed to be 80%. The first recycle stream location was two stages above the first middle effluent location. The results are given below. Clearly, the concentration of 3-cyclohexenone in the cyclohexanone product (stream 227) was reduced by only a small percentage compared to the feed stream (stream 203). The high concentrations of 3-cyclohexenone in both streams 227 and 229 may render them unsuitable for intended uses.

| Stream | Concentration of 3-cyclohexenone (ppm) |
|---|---|
| Feed Stream (Stream 203) | 104 |
| Cyclohexanone Product (Stream 227) | 85 |
| KA Oil Product (Stream 229) | 33 |

Example 3

(Inventive)

Figure 3:
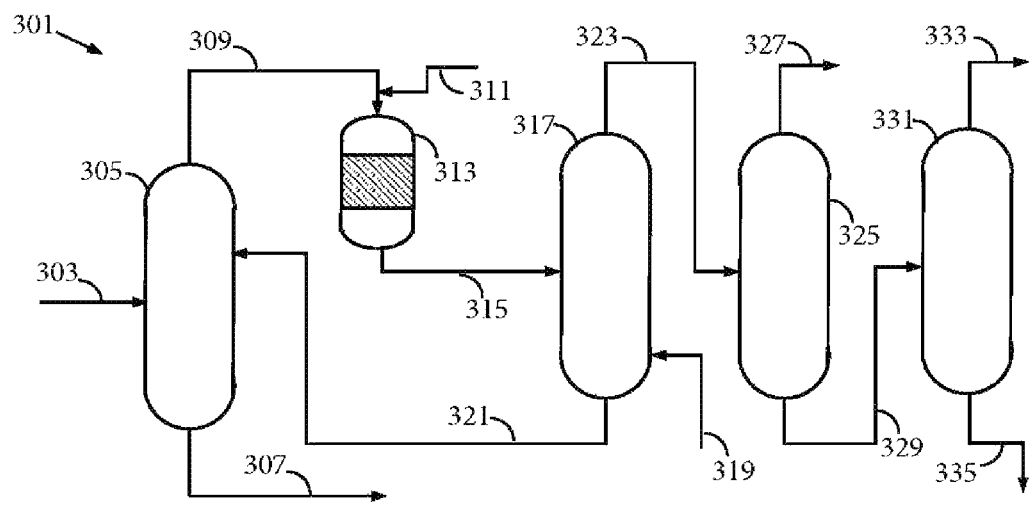
FIG. 3 is a schematic diagram showing an inventive process/system including a primary fractionator, a phenol hydrogenation reactor, and additional distillation columns, resulting in low concentration of 3-cyclohexenone in the cyclohexanone product.

FIG. 3 schematically illustrates a process/system 301 operating to produce cyclohexanone from a first feed mixture comprising cyclohexylbenzene, phenol, cyclohexanone, water, light acids, 2-cyclohexenone, and 3-cyclohexenone. The first feed mixture stream 303 is fed into a first distillation column (aka "primary fractionator") 305 at a first feed mixture feeding location, where a lower effluent stream 307 (preferably in the vicinity of the bottom of column 305) comprising cyclohexylbenzene and other optional heavy components is produced. Stream 307 can be further separated to obtain a substantially pure stream of cyclohexylbenzene, which is then recycled to an upstream oxidation reactor (not shown) where cyclohexylbenzene is oxidized to form cyclohexylbenzene hydroperoxide. From column 305, a first upper effluent 309 is drawn at a first upper effluent location above the first feed mixture location, preferably in the vicinity of the top of column 305. Stream 309, comprising cyclohexanone, phenol, cyclohexanol, 2-cyclohexenone, 3-cyclohexenone, and optionally cyclohexylbenzene and bicyclohexane, is then fed into a hydrogenation reactor 313 together with a stream of hydrogen 311. In the presence of a bed of hydrogenation catalyst installed inside reactor 313, 2-cyclohexenone, 3-cyclohexenone, and phenol undergo hydrogenation reactions to form cyclohexanone, cyclohexanone undergoes hydrogenation to form cyclohexanol, and the optional cyclohexylbenzene, if present, undergoes hydrogenation form bicyclohexane. Because hydrogenation of 2-cyclohexenone and 3-cyclohexenone are much faster than phenol hydrogenation under typical phenol hydrogenation conditions in the presence of the phenol hydrogenation catalyst, the hydrogenation reactor effluent 315 comprises cyclohexanone and cyclohexanol at higher concentrations than stream 309, phenol at a reduced concentration than stream 309, and optionally cyclohexylbenzene and bicyclohexane, and is depleted in (preferably substantially free) of 2-cyclohexenone and 3-cyclohexenone because both are substantially converted to cyclohexanone. Stream 315 is supplied to a second distillation column 317, where a cyclohexanone-rich upper effluent stream 323 (preferably at a location in the vicinity of the top of column 317) and a phenol-rich lower effluent stream 321 are obtained (preferably at a location in the vicinity of the bottom of column 317). A hydrogen stream 319 is preferably (though not required to be) supplied to the second distillation column 317 (preferably at a location in the vicinity of the bottom of the column). Hydrogen gas travelling upward along column 317 facilitates the separation of phenol from cyclohexanone/cyclohexanol and leads to energy savings in the process. Stream 321, comprising cyclohexanone at a concentration lower than stream 315, phenol at a concentration higher than stream 315, and optional cyclohexylbenzene and bicyclohexane, depleted in (preferably substantially free of) 2-cyclohexenone and 3-cyclohexenone, is recycled back to the first distillation column 305 at a second feeding location higher than the first feeding location and lower than the first upper effluent location. Alternatively, stream 321 may be recycled in its entirety to the hydrogenation reactor 313. If cyclohexylbenzene is present in stream 309, doing so would result in accumulation of bicyclohexane in stream 321, which can be undesirable. Alternatively, one can recycle a portion of stream 321 to the hydrogenation reactor, and another portion to the first distillation column as described above.

Stream 323, comprising cyclohexanone, cyclohexanol, water, and other lights such as light acids and hydrogen, depleted of 2-cyclohexenone and 3-cyclohexenone and preferably substantially free of 2-cyclohexenone and 3-cyclohexenone, is then fed into a third distillation column 325, where it is separated into an light component-rich upper effluent stream 327 comprising hydrogen, water, light acids, and the like, and a cyclohexanone-rich lower effluent stream 329. Stream 327 can be further separated (not shown) to obtain a stream of hydrogen, which can be recycled to the hydrogenation reactor 313 as at least a part (preferably the entirety) of the hydrogen stream 311 supplied into the hydrogenation reactor. Alternatively or in addition, one could also choose to separate stream 323 before it is fed into column 325 via high pressure separation drum as in conventional hydro-processing to obtain a stream of hydrogen, which can be supplied to the hydrogenation reactor.

Stream 329 is then fed into a fourth distillation column 331, where it is separated into a cyclohexanone upper effluent stream 333 and a lower effluent stream 335. Stream 333 can comprise cyclohexanone at a purity of higher than 99 wt %, preferably higher than 99.5 wt %, more preferably higher than 99.9 wt %. Stream 329 may comprise 2-cyclohexenone and/or 3-cyclohexeneone, each independently at a concentration in the range from 0.01 to 20 (preferably 0.01 to 10 ppm, more preferably 0.01 to 5 ppm, still more preferably 0.01 to 1) ppm by weight, based on the total weight of stream 335. Stream 335 can comprise cyclohexanol at any concentration depending on the degree of separation in the fourth distillation column, but preferably in the range from 0 to 90 wt %, more preferably from 10 to 60 wt %. Streams 333 and 335 can be delivered to product storage and used for downstream applications such as productions of caprolactam, adipic acid, and the like. Stream 335, if containing cyclohexanol at substantial quantity, can be either sold and used as a KA oil product, or dehydrogenated to make an additional quantity of high-purity cyclohexanone.

In FIG. 3, a single first upper effluent 309 comprising phenol, cyclohexanone, cyclohexanol, 2-cyclohexenone, 3-cyclohexenone, and light components is drawn from column 305. Alternatively, two upper effluent may be drawn from column 305: a first upper effluent, preferably liquid, comprising cyclohexanone, phenol, 2-cyclohexenone, 3-cyclohexenone, and cyclohexanol and substantially free of water and other light components, and a second upper effluent comprising cyclohexanone, water, and other light components. The second upper effluent, preferably withdrawn at a location in the vicinity of the top of column 305, can be separated to obtain (i) a cyclohexanone-rich stream, which is then recycled to a location preferably in the vicinity of the top of column 305, and (ii) a light component stream, which can be further treated and disposed as waste. The first upper effluent is then fed into the hydrogenation reactor as stream 309.

In FIG. 3, stream 321 is shown to be recycled in its entirety to column 305. Alternatively, one can split this stream into two fractions, one recycled to the column 305 as shown, the other to the hydrogenation reactor (not shown), to increase the overall conversion of phenol in the hydrogenation reactor. While theoretically it is possible to recycle stream 321 in its entirety to the hydrogenation reactor, doing so can result in the accumulation of heavy components such as cyclohexylbenzene and bicyclohexane in the hydrogenation reactor, which can reduce overall process efficiency and therefore can be undesirable.

In FIG. 3, two distillation columns 325 and 331 are utilized to separate stream 323 to obtain light component effluent stream 327, the cyclohexanone effluent stream 333 and the lower effluent stream 335 (which can be a KA oil stream). Alternatively, the two columns can be combined into a single column, with the light component effluent drawn preferably in the vicinity of the top, the lower effluent (e.g., a KA oil effluent) drawn preferably in the vicinity of the bottom, and the cyclohexanone effluent drawn at a location in between the two, preferably higher than the first feeding location.

Example 4

Figure 4:
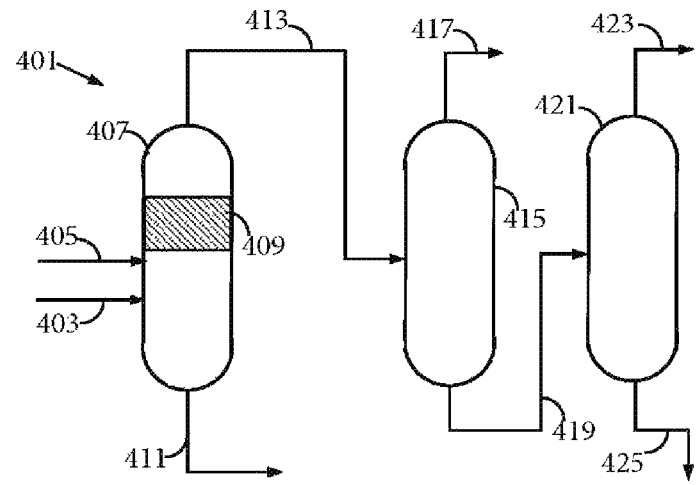
FIG. 4 is a schematic diagram showing another inventive process/system including a reactive distillation column performing both the functions of a hydrogenation reactor and a primary fractionator, and additional distillation columns, resulting in low concentration of 3-cyclohexenone in the cyclohexanone product.

FIG. 4 schematically illustrates a process/system 401 operating to produce cyclohexanone from a first feed mixture comprising cyclohexylbenzene, phenol, cyclohexanone, water, light acids, 2-cyclohexenone, and 3-cyclohexenone. Process/system 401 comprises a hydrogenation zone 409 having a bed of hydrogenation catalyst installed inside the first distillation column 407. The first feed mixture stream 403 is fed into a first distillation column 407 at a first feed mixture feeding location below the hydrogenation zone 409. As shown in FIG. 4, a hydrogen stream 405 is supplied to the first distillation column at a location below the hydrogenation zone and above the first feed location, although in addition or instead hydrogen stream 405 can be supplied at a location below the first feeding location as well. Preferably, in the vicinity of the bottom of column 407, a lower effluent stream 411 comprising cyclohexylbenzene and other optional heavy components is obtained. The location of the hydrogenation zone 409 is chosen such that hydrogen, water, other light components, cyclohexanone, cyclohexanol, and phenol enter into the hydrogenation zone. Preferably, only minor amount of or no cyclohexylbenzene (e.g., at most 5% of all cyclohexylbenzene in feed mixture stream 403) enters the hydrogenation zone. The height of the hydrogenation zone, the hydrogenation catalyst, the hydrogenation conditions, and the length and condition of the column portion above the hydrogenation zone are chosen such that the overall conversion of phenol in the hydrogenation zone is generally in the range from 90% to 100%, preferably above 99%, in column 407. Similarly, because 2-cyclohexenone and 3-cyclohexenone hydrogenate at much higher rate than phenol, they are substantially completely converted. Thus, a first upper effluent stream 413 substantially free of phenol, 2-cyclohexenone and 3-cyclohexenone, and comprising cyclohexanone, cyclohexanol, water and other light components is obtained at a location above the hydrogenation zone (preferably from a location in the vicinity of the top of column 407).

Stream 413 is then fed into a second distillation column 415, where it is separated into a light component-rich upper effluent stream 417 comprising hydrogen, water, light acids, and the like, and a cyclohexanone-rich lower effluent stream 419. Stream 417 can be further separated (not shown) to obtain a stream of hydrogen by means such as high-pressure separation drum used in conventional hydro-processing processes, which can be recycled to the first distillation column 407 as a part of the hydrogen stream 405 supplied into column 407.

Stream 419 is then fed into a fourth distillation column 421, where it is separated into a cyclohexanone-rich upper effluent stream 423 and a lower effluent stream 425. Stream 423 can comprise cyclohexanone at a purity of higher than 99 wt %, preferably higher than 99.5 wt %, more preferably higher than 99.9 wt %. Stream 425 can comprise cyclohexanol at any concentration, depending on the degree of hydrogenation carried out in the hydrogenation zone, but preferably in the range from 0 to 90 wt %, more preferably from 10 to 40 wt %. Streams 423 and 425 can be delivered to product storage and used for downstream applications such as productions of caprolactam, adipic acid, and the like. Because stream 413 is depleted in 2-cyclohexenone and 3-cyclohexenone and preferably substantially free of both, streams 419, 423, and 425 are likewise depleted in both and preferably substantially free of both. Stream 425, if containing cyclohexanol at substantial quantity, can be either sold and used as a KA oil product, or dehydrogenated to make additional quantity of high-purity cyclohexanone.

In FIG. 4, two distillation columns 415 and 421 are utilized to separate stream 413 to obtain light component effluent stream 417, the cyclohexanone-rich upper effluent stream 423 and the lower effluent stream 425 (which can be a KA oil stream). Alternatively, the two columns can be combined into a single column, with the light component effluent (preferably drawn in the vicinity of the top), the lower effluent (e.g., a KA oil stream) drawn preferably in the vicinity of the bottom, and the cyclohexanone effluent drawn at a location in between the two, preferably higher than the location where stream 413 is fed into the distillation column.

Example 5

(Inventive)

Figure 5:
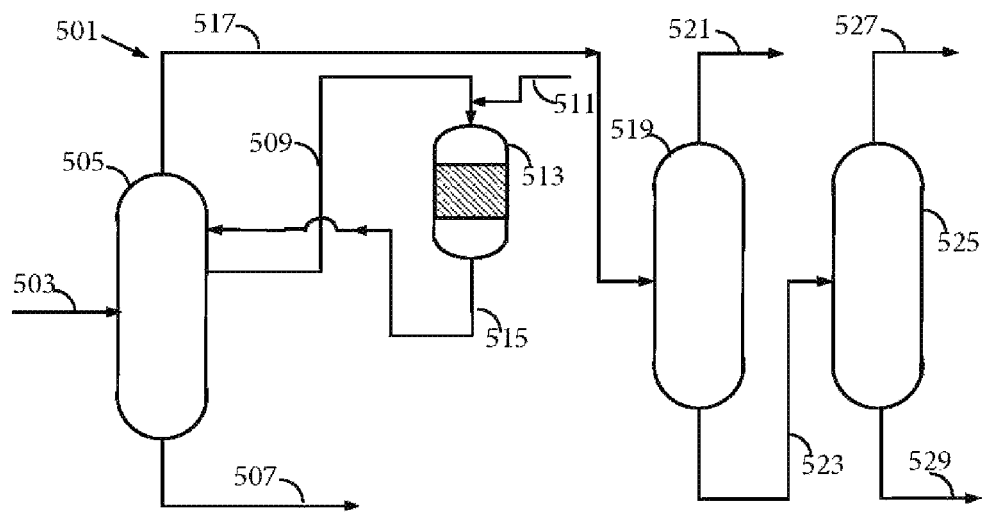
FIG. 5 is a schematic diagram showing yet another inventive process/system including a primary fractionator, a hydrogenation reactor, and additional distillation columns, with specialized configuration resulting in low concentration of 3-cyclohexenone in the cyclohexanone product.

FIG. 5 schematically illustrates a process/system 501 operating to produce cyclohexanone from a first feed mixture comprising cyclohexylbenzene, phenol, cyclohexanone, water, light acids, 2-cyclohexenone, and 3-cyclohexenone. The first feed mixture stream 503 is fed into a first distillation column 505 at a first feed mixture feeding location, where a lower effluent stream 507 preferably in the vicinity of the bottom of column 505 comprising cyclohexylbenzene, bicyclohexane, and other optional heavy components is produced. Stream 507 can be further separated to obtain a substantially pure stream of cyclohexylbenzene and then recycled to an upstream oxidation reactor (not shown) where cyclohexylbenzene is oxidized to form cyclohexylbenzene hydroperoxide. From column 505, a middle effluent 509 is drawn at a middle effluent location above the first feed mixture location, but below the top of column 505. Stream 509, comprising cyclohexanone, phenol, cyclohexanol, 3-cyclohexenone, optionally cyclohexylbenzene, optionally bicyclohexane, and optionally 2-cyclohexenone, is then fed into a hydrogenation reactor 513 together with a stream of hydrogen 511. In the presence of a bed of hydrogenation catalyst installed inside reactor 513, 2-cyclohexenone, 3-cyclohexenone, and phenol undergo hydrogenation reactions to form cyclohexanone, cyclohexanone undergoes hydrogenation to form cyclohexanol, and the optional cyclohexylbenzene, if present, undergoes hydrogenation to form bicyclohexane. Hydrogenation of 2-cyclohexenone and 3-cyclohexenone are believed to be much faster than phenol hydrogenation under typical phenol hydrogenation conditions in the presence of the phenol hydrogenation catalyst. As such, the hydrogenation reactor effluent 515 comprises cyclohexanone and cyclohexanol at higher concentrations than stream 509, phenol at a reduced concentration than stream 509, and optional cyclohexylbenzene and bicyclohexane, and is depleted in (preferably substantially free) of 2-cyclohexenone and 3-cyclohexenone. Stream 515 is recycled back to the first distillation column 505 at a first recycle stream location above the first middle effluent location, where it is further separated. Above the first recycle stream location, an upper effluent 517 is produced at a location preferably in the vicinity of the top of column 505. One can also separate stream 515 using convention hydro-processing equipment such as high-pressure separation drum to obtain a hydrogen stream, which can be supplied to the hydrogenation reactor as a portion of hydrogen stream 511.

Stream 517 comprises cyclohexanone, cyclohexanol, water, and other light components such as light acids and is substantially free of phenol. As demonstrated in Example 1, 3-cyclohexenone cannot be separated from cyclohexanone using simple, conventional distillation. To reduce the amount of 3-cyclohexenone in stream 517, the present inventors have found that, by (i) controlling the recycle location to be in the range from 6 to 30, preferably from 10 to 25, more preferably from 10 to 20, still more preferably from 10 to 18, still more preferably 10 to 15, stages above the middle effluent location, and preferably but not necessarily also (ii) operating the hydrogenation reactor at a phenol conversion no greater than 80% (or no greater than 70%, 60%, 50%, or even 40%, preferably in the range from 30% to 70%, more preferably in the range from 35% to 60%, still more preferably in the range from 40% to 50%), and preferably but not necessarily also (iii) controlling the flow rate of stream 509, one can substantially suppress the upward travel of 3-cyclohexenone to beyond the recycle location, and channel substantially all 3-cyclohexenone into the first middle effluent 509 where it is then desirably substantially completely hydrogenated. In general, a higher flow rate of stream 509 favors the suppression of the upward travel of 3-cyclohexenone. At high phenol conversions higher than 80%, flow rate at stream 509 must be substantially increased, reducing the phenol concentration in the hydrogenation reactor and increasing energy usage.

Without intending to be bound by a particular theory, it is believed that such configuration of column 505 and the hydrogenation reactor 513 results in substantial quantity of liquid supplied into column 505 via stream 515, a significant portion of which travels downwards to trap substantially all of the 3-cyclohexenone in the zone between the middle effluent location and the recycle location, the preferential distribution of 3-cyclohexenone in the middle effluent 509 and subsequent abatement thereof via hydrogenation in hydrogenation reactor 513.

Stream 517, substantially free of phenol and 3-cyclohexenone, is then supplied to a second distillation column 519, where it is separated to obtain a light component-rich upper stream 521 comprising water, and light acids, and a cyclohexanone-rich lower effluent stream 523 comprising cyclohexanone and cyclohexanol.

Stream 523 is then fed into a third distillation column 525, where it is separated into a cyclohexanone upper effluent stream 527 and a lower effluent stream 529. Stream 527 can comprise cyclohexanone at a purity of higher than 99 wt %, preferably higher than 99.5 wt %, more preferably higher than 99.9 wt %. Stream 529 can comprise cyclohexanol at any concentration depending on the degree of separation in the third distillation column, but preferably in the range from 0 to 90 wt %, more preferably from 10 to 40 wt %. Streams 527 and 529 can be delivered to product storage and used for downstream applications such as productions of caprolactam, adipic acid, and the like. Stream 529, if containing cyclohexanol at substantial quantity, can be either sold and used as a KA oil product, or dehydrogenated to make additional quantity of high-purity cyclohexanone.

In FIG. 5, two distillation columns 519 and 525 are utilized to separate stream 517 to obtain light component effluent stream 521, the cyclohexanone effluent stream 527 and the lower effluent stream 529 (which can be a KA oil stream). Alternatively, the two columns can be combined into a single column, with the light component effluent drawn preferably in the vicinity of the top, the KA-oil effluent drawn preferably in the vicinity of the bottom, and the cyclohexanone effluent drawn in the middle.

Assuming a phenol conversion of 30% in phenol hydrogenation, a steady state process simulation using Schneider Electric Software SimSci Pro/II of this configuration was performed. 3-cyclohexenone was assumed to react at 100% conversion to cyclohexanone across the hydrogenation reactor. Ten (10) theoretical stages were assumed between stream 509 and 515. The feed mixture 503 comprised 25 wt % phenol, 25 wt % cyclohexanone, 42 wt % cyclohexylbenzene, 100 ppm 3-cyclohexenone, and 0 to 8 wt % other impurities. The 3-cylohexenone concentration in feed and product streams is given below. As can be seen, concentrations of 3-cyclohexenone in both the cyclohexanone product stream (stream 527) and stream 529 are exceedingly low, much lower than its concentration in feed mixture stream 503, indicating substantially complete and highly effective abatement of 3-cyclohexenone in the process. This is in stark contrast to the result in comparative Example 2 above, where the first recycle stream location was only 2 stages above the first middle effluent location. Stream 527, with such low concentration of 3-cyclohexenone, can be advantageously used for the production of high-quality caprolactam for use in making nylon-6. Stream 529, with its low concentration of 3-cyclohexenone, can be advantageously used for the production of high-quality adipic acid, and the like, for use in making nylon-6,6, and the like.

| Stream | Concentration of 3-cyclohexenone (ppm) |
|---|---|
| Feed Mixture (Stream 503) | 100.1 |
| Cyclohexanone Product (Stream 527) | 0.36 |
| Lower Effluent (Stream 529) | 0.15 |

Example 6

A mixture comprising 39 wt % phenol, 56 wt % cyclohexanone, 0.1 wt % cyclohexanol, 3686 ppm by weight of 2-cyclohexenone, and an undetermined concentration of 3-cyclohexenone was passed through a hydrogenation reactor with a stream of hydrogen in the presence of a hydrogenation catalyst operating at a pressure of 34 psi (234 kPa, gauge) and at 150° C. Analyses of the feed and the hydrogenated effluent showed that both 2-cyclohexenone and 3-cyclohexenone were substantially all converted and resulted in a concentration of 3-cyclohexenone in the hydrogenated mixture of no higher than 20 ppm (or even no higher than 10 ppm) by weight, and a total concentration of 2-cyclohexenone and 3-cyclohexenone combined of no higher than 20 ppm (or even no higher than 10 ppm) by weight, based on the total weight of the hydrogenated effluent.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The contents of all references cited herein are incorporated by reference in their entirety.

The invention claimed is:

1. A process for producing cyclohexanone from a first feed mixture comprising cyclohexylbenzene, cyclohexanone, phenol, and 3-cyclohexenone, the process comprising:
   feeding the first feed mixture into a first distillation column at a first feeding location on the first distillation column;
   obtaining a lower cyclohexylbenzene-rich effluent from the first distillation column;
   obtaining a first upper effluent from a first upper effluent location on the first distillation column above the first feeding location, the first upper effluent comprising cyclohexanone, cyclohexanol, and is substantially free of phenol and 3-cyclohexenone;
   obtaining a middle effluent from a middle effluent location on the first distillation column above the first feeding location and below the first upper effluent location, the middle effluent comprising cyclohexanone, phenol, and 3-cyclohexenone;

feeding at least a portion of the middle effluent to a hydrogenation reactor, where the middle effluent contacts with hydrogen in the presence of a hydrogenation catalyst under hydrogenation conditions to produce a hydrogenation reactor effluent substantially free of 3-cylcohexenone;

feeding at least a portion of the hydrogenation reactor effluent to the first distillation column at a recycle location between the middle effluent location and the first upper effluent location, wherein:

the recycle location is 6 to 30 stages above the middle effluent location; and the conversion of phenol in the hydrogenation reactor is no higher than 99%.

2. The process of claim 1, wherein:

the concentration of 3-cyclohexenone in the first feed mixture is in the range from 30 ppm by weight to 1 wt %, based on the total weight of the first feed mixture;

the first feed mixture optionally comprises 2-cyclohexenone at a concentration in the range from 30 ppm by weight to 1 wt %, based on the total weight of the first feed mixture; and the hydrogenation reactor effluent is substantially free of 2-cyclohexenone.

3. The process of claim 1, wherein in the hydrogenation reactor, the conversion of 3-cyclopexenone is at least 95%, and the conversion of the optional 2-cyclohexenone, if present, is at least 95%.

4. The process of claim 1, wherein the recycle location is 10 to 20 stages above the middle effluent location.

5. The process of claim 1, wherein in the hydrogenation reactor, the conversion of phenol is in the range from 30 to 99%.

6. The process of claim 5, wherein in the hydrogenation reactor, the conversion of phenol is in the range from 40 to 80%.

7. The process of claim 1, wherein:

the hydrogenation catalyst comprises at least one of the following elements: Fe, Co, Ni, Ru, Rh, Pd, Re, Os, Ir, and Pt; and the hydrogenation conditions comprise a temperature in the range from 25° C. to 300° C. and a hydrogen partial pressure in the range from 50 to 2000 kPa (absolute pressure).

8. The process of claim 1, further comprising feeding at least a portion of the hydrogenation reactor effluent to the hydrogenation reactor.

9. The process of claim 1, wherein the first feed mixture further comprises water and light acids, the first middle effluent comprises water and light acids, and the first middle effluent is stripped of water and/or light acids before being fed into the hydrogenation reactor.

10. The process of claim 1, wherein the first feed mixture comprises water and light acids, and the process further comprises obtaining a second upper effluent from the first distillation column at a second upper effluent location above the first upper effluent location, wherein the second upper effluent comprises water and light acids, and is substantially free of phenol.

11. The process of claim 10, wherein the second upper effluent further comprises cyclohexanone, and the process further comprises:

separating at least a portion of the cyclohexanone from the second upper effluent to obtain a recycle cyclohexanone stream; and recycling at least a portion of the recycle cyclohexanone stream to the first distillation column at a location below the second upper effluent location.

12. The process of claim 1, further comprising:

feeding at least a portion of the first upper effluent into a second distillation column;

obtaining an light-components-rich upper effluent from the second distillation column;

obtaining a light-components-depleted lower effluent from the second distillation column;

feeding at least a portion of the light-components-depleted effluent into a third distillation column; and obtaining a cyclohexanone-rich upper effluent and a lower effluent from the third distillation column.

13. The process of claim 12, wherein the lower effluent from the third distillation column is a KA oil effluent comprising cyclohexanol at a concentration in the range from 10 to 40 wt %, based on the total weight of the KA oil effluent.

14. The process of claim 12, wherein the lower effluent from the third distillation column comprises cyclohexanol and cyclohexanone, and the lower effluent is further subject to dehydrogenation to convert at least a portion of the cyclohexanol to cyclohexanone.

15. The process of claim 12, wherein the cyclohexanone-rich upper effluent from the third distillation column comprises 3-cyclohexenone at a concentration no greater than 20 ppm by weight, based on the total weight of the cyclohexanone-rich upper effluent, and the lower effluent from the third distillation column comprises 3-cyclohexenone at a concentration no greater than 20 ppm by weight, based on the total weight of the lower effluent from the third distillation column.

16. The process of claim 12, wherein the cyclohexanone-rich upper effluent from the third distillation column comprises 2-cyclohexenone at a concentration no greater than 20 ppm by weight, based on the total weight of the cyclohexanone-rich upper effluent, and the lower effluent from the third distillation column comprises 2-cyclohexenone at a concentration no greater than 20 ppm by weight, based on the total weight of the lower effluent from the third distillation column.

17. The process of claim 12, wherein the cyclohexanone-rich upper effluent from the third distillation column comprises 2-cyclohexenone ad 3-cyclohexenone in total at a concentration no greater than 20 ppm by weight, based on the total weight of the cyclohexanone-rich upper effluent, and the lower effluent from the third distillation column comprises 2-cyclohexenone and 3-cyclohexenone in total at a concentration no greater than 20 ppm by weight, based on the total weight of the lower effluent from the third distillation column.

18. The process of claim 12, wherein the cyclohexanone-rich upper effluent from the third distillation column comprises 2-cyclohexenone and 3-cyclohexenone in total at a concentration no greater than 10 ppm by weight, based on the total weight of the cyclohexanone-rich upper effluent, and the lower effluent from the third distillation column comprises 2-cyclohexenone and 3-cyclohexenone in total at a concentration no greater than 10 ppm by weight, based on the total weight of the lower effluent from the third distillation column.

19. The process of claim 1, wherein the first feed mixture comprises cyclohexylbenzene at a concentration in the range from 20 to 70 wt %, cyclohexanone at a concentration in the range from 10 to 40 wt %, phenol at a concentration in the range from 10 to 40 wt %, 3-cyclohexenone at a concentration in the range from 30 ppm by weight to 1 wt %, and 2-cyclohexenone at a concentration in the range from 30 ppm by weight to 1 wt %, based on the total weight of the first feed mixture.

20. The process of claim 1, wherein the first feed mixture is produced by a process comprising:
  contacting benzene with hydrogen in a hydroalkylation reactor in the presence of a hydroalkylation catalyst to produce a hydroalkylation mixture comprising cyclohexylbenzene;
  oxidizing at least a portion of the cyclohexylbenzene to obtain an oxidized mixture comprising cyclohexylbenzene hydroperoxide and cyclohexylbenzene;
  contacting at least a portion of the oxidized mixture with an acid in a cleavage reactor to obtain a cleavage mixture comprising phenol, cyclohexanone, and 3-cyclohexenone; and
  obtaining the first feed mixture from the cleavage effluent.

* * * * *